US012735734B2

(12) United States Patent
Jewett et al.

(10) Patent No.: US 12,735,734 B2
(45) Date of Patent: Sep. 15, 2026

(54) LOW-COST, THERMOSTABLE, LYOPHILIZED, CELL-FREE PROTEIN SYNTHESIS PLATFORM

(71) Applicant: Northwestern University, Evanston, IL (US)

(72) Inventors: Michael Christopher Jewett, Evanston, IL (US); Katherine F. Warfel, Evanston, IL (US)

(73) Assignee: Northwestern University, Evanston, IL (US)

( * ) Notice: Subject to any disclaimer, the term of this patent is extended or adjusted under 35 U.S.C. 154(b) by 275 days.

(21) Appl. No.: 18/292,604

(22) PCT Filed: Jul. 27, 2022

(86) PCT No.: PCT/US2022/074212
§ 371 (c)(1),
(2) Date: Jan. 26, 2024

(87) PCT Pub. No.: WO2023/010053
PCT Pub. Date: Feb. 2, 2023

(65) Prior Publication Data

US 2025/0043324 A1 Feb. 6, 2025

Related U.S. Application Data

(60) Provisional application No. 63/241,799, filed on Sep. 8, 2021, provisional application No. 63/203,709, filed on Jul. 28, 2021.

(51) Int. Cl.
*C12N 1/06* (2026.01)
*A61P 37/00* (2006.01)
*C12P 21/00* (2006.01)

(52) U.S. Cl.
CPC .................................. *C12P 21/005* (2013.01)

(58) Field of Classification Search
CPC .......... C12N 1/06; A61P 37/00; C12P 21/005; C12P 21/00
See application file for complete search history.

(56) References Cited

U.S. PATENT DOCUMENTS

| | | | |
|---|---|---|---|
| 4,458,066 | A | 7/1984 | Caruthers |
| 4,683,195 | A | 7/1987 | Mullis et al. |
| 4,683,202 | A | 7/1987 | Mullis |
| 5,478,730 | A | 12/1995 | Alakhov et al. |
| 5,494,810 | A | 2/1996 | Barany et al. |
| 5,556,769 | A | 9/1996 | Lyubov et al. |
| 5,665,563 | A | 9/1997 | Beckler |
| 6,168,931 | B1 | 1/2001 | Swartz |
| 6,548,276 | B2 | 4/2003 | Swartz |
| 6,869,774 | B2 | 3/2005 | Endo et al. |
| 6,905,843 | B1 | 6/2005 | Endo et al. |
| 6,994,986 | B2 | 2/2006 | Swartz |
| 7,118,883 | B2 | 10/2006 | Inoue et al. |
| 7,186,525 | B2 | 3/2007 | Sakanyan et al. |
| 7,189,528 | B2 | 3/2007 | Higashide et al. |
| 7,235,382 | B2 | 6/2007 | Endo |
| 7,338,789 | B2 | 3/2008 | Swartz |
| 7,387,884 | B2 | 6/2008 | Suzuki et al. |
| 7,396,664 | B2 | 7/2008 | Daly et al. |
| 7,399,610 | B2 | 7/2008 | Shikata et al. |
| 7,776,535 | B2 | 8/2010 | Mehl |
| 7,817,794 | B2 | 10/2010 | Galvin |
| 8,298,759 | B2 | 10/2012 | Voloshin |
| 8,703,471 | B2 | 4/2014 | Aebi |
| 8,715,958 | B2 | 5/2014 | Goerke |
| 8,734,856 | B2 | 5/2014 | Endo |
| 8,999,668 | B2 | 4/2015 | DeLisa et al. |
| 9,005,920 | B2 | 4/2015 | Kusumegi |
| 2004/0209321 | A1 | 10/2004 | Swartz |
| 2005/0054044 | A1 | 3/2005 | Swartz et al. |
| 2005/0153390 | A1 | 7/2005 | Endo et al. |
| 2005/0170452 | A1 | 8/2005 | Wildt et al. |
| 2006/0211085 | A1 | 9/2006 | Bobrowicz |
| 2006/0234345 | A1 | 10/2006 | Schwartz |
| 2006/0252672 | A1 | 11/2006 | Betenbaugh et al. |
| 2006/0257399 | A1 | 11/2006 | Gerngross et al. |
| 2006/0286637 | A1 | 12/2006 | Hamilton |
| 2007/0026485 | A1 | 2/2007 | DeFrees et al. |
| 2007/0154983 | A1 | 7/2007 | Calhoun et al. |
| 2007/0178551 | A1 | 8/2007 | Gerngross |
| 2008/0138857 | A1 | 6/2008 | Swartz |
| 2012/0171720 | A1 | 7/2012 | Church |

(Continued)

FOREIGN PATENT DOCUMENTS

| | | | |
|---|---|---|---|
| CN | 111378707 | A | 7/2020 |
| WO | 2003056914 | A2 | 7/2003 |

(Continued)

OTHER PUBLICATIONS

Anderson, M. J., Stark, J. C., Hodgman, C. E. & Jewett, M. C. Energizing eukaryotic cell-free protein synthesis with glucose metabolism. FEBS Lett. 589, 1723-1727 (2015).
Beaucage, S. L., and Marvin H. Caruthers. "Deoxynucleoside phosphoramidites—a new class of key intermediates for deoxypolynucleotide synthesis." Tetrahedron letters 22.20 (1981): 1859-1862.
Brown, Eugene L., et al. "[8] Chemical synthesis and cloning of a tyrosine tRNA gene." Methods in Enzymology. vol. 68. Academic Press, 1979. 109-151.
Zipursky, S. et al. Benefits of using vaccines out of the cold chain: delivering meningitis A vaccine in a controlled temperature chain during the mass immunization campaign in Benin. Vaccine 32, 1431-1435 (2014).
Cai, Q. et al. A simplified and robust protocol for immunoglobulin expression in *Escherichia coli* cell-free protein synthesis systems. Biotechnol. Prog. 31, 823-831 (2015).

(Continued)

*Primary Examiner* — Maryam Monshipouri
(74) *Attorney, Agent, or Firm* — Quarles & Brady LLP

(57) ABSTRACT

The present disclosure relates to stable, cost-effective, cell-free systems, compositions, methods, and kits for bio-manufacturing proteins. The systems, methods, and kits allow for cell-free bio-manufacturing of desired products in cell-free conditions, wherein the system can be stably stored or transported, in lyophilized form, at temperatures up to 50° C. for several weeks prior to use.

12 Claims, 20 Drawing Sheets

(56) References Cited

U.S. PATENT DOCUMENTS

| | | | |
|---|---|---|---|
| 2014/0045267 | A1 | 2/2014 | Lajoie et al. |
| 2014/0255987 | A1 | 9/2014 | DeLisa |
| 2014/0295492 | A1 | 10/2014 | Jewett et al. |
| 2014/0349353 | A1 | 11/2014 | Nomura et al. |
| 2015/0259757 | A1 | 9/2015 | Jewett et al. |
| 2016/0060301 | A1 | 3/2016 | Jewett et al. |
| 2017/0349928 | A1 | 12/2017 | Jewett et al. |
| 2018/0016612 | A1 | 1/2018 | Jewett et al. |
| 2018/0016614 | A1 | 1/2018 | Jewett |
| 2020/0299745 | A1 | 9/2020 | Chandler et al. |
| 2020/0299789 | A1 | 9/2020 | Lee et al. |

FOREIGN PATENT DOCUMENTS

| | | | |
|---|---|---|---|
| WO | 2004013151 | A2 | 2/2004 |
| WO | 2004035605 | A2 | 4/2004 |
| WO | 2006102652 | A2 | 9/2006 |
| WO | 2006119987 | A2 | 11/2006 |
| WO | 2007120932 | A2 | 10/2007 |
| WO | 2020146814 | A1 | 7/2020 |

OTHER PUBLICATIONS

Zubi, Y. S. et al. Metal-Responsive Regulation of Enzyme Catalysis using Genetically Encoded Chemical Switches. ChemRxiv (2021) doi:10.33774/chemrxiv-2021-9ql74.

Calhoun, K. A. & Swartz, J. R. Energizing cell-free protein synthesis with glucose metabolism. Biotechnol. Bioeng. 90, 606-613 (2005).

Calhoun, K. A.; Swartz, J. R. An Economical Method for Cell-Free Protein Synthesis Using Glucose and Nucleoside Monophosphates. Biotechnol. Prog. 2005. https://doi.org/10.1021/bp050052y.

Caschera, F.; Noireaux, V. A Cost-Effective Polyphosphate-Based Metabolism Fuels an All *E. coli* Cell-Free Expression System. Metab. Eng. 2015, 27, 29-37. https://doi.org/10.1016/J.YMBEN.2014.10.007.

Caschera, F.; Noireaux, V. Synthesis of 2.3 Mg/Ml of Protein with an All *Escherichia coli* Cell-Free Transcription-Translation System. Biochimie 2014. https://doi.org/10.1016/j.biochi.2013.11.025.

Çelik, E. et al. Glycoarrays with engineered phages displaying structurally diverse oligosaccharides enable high-throughput detection of glycan-protein interactions. Biotechnol. J. 10, 199-209 (2015).

Chang, L. L. & Pikal, M. J. Mechanisms of protein stabilization in the solid state. J. Pharm. Sci. 98, 2886-2908 (2009).

Chen, L. et al. Outer membrane vesicles displaying engineered glycotopes elicit protective antibodies. Proc. Natl. Acad. Sci. U. S. A. 113, E3609-18 (2016).

Chen, Z. et al. De novo design of protein logic gates. Science 368, 78-84 (2020).

Thavarajah, W. et al. Point-of-Use Detection of Environmental Fluoride via a Cell-Free Riboswitch-Based Biosensor. ACS Synth. Biol. 9, 10-18 (2020).

Trotter, C. L. et al. Optimising the use of conjugate vaccines to prevent disease caused by Haemophilus influenzae type b, *Neisseria meningitidis* and *Streptococcus pneumoniae*. Vaccine 26, 4434-4445 (2008).

Goodchild, John. "Conjugates of oligonucleotides and modified oligonucleotides: a review of their synthesis and properties." Bioconjugate Chemistry 1.3 (1990): 165-187.

Gregorio, N. E.; Kao, W. Y.; Williams, L. C.; Hight, C. M.; Patel, P.; Watts, K. R.; Oza, J. P. Unlocking Applications of Cell-Free Biotechnology through Enhanced Shelf Life and Productivity of *E. coli* Extracts. ACS Synth. Biol. 2020, 9 (4), 766-778. https://doi.org/10.1021/acssynbio.9b00433.

Guarino, C., & DeLisa, M. P. (2012). A prokaryote-based cell-free translation system that efficiently synthesizes glycoproteins. Glycobiology, 22(5), 596-601.

Guzman-Chavez, F. et al. Constructing Cell-Free Expression Systems for Low-Cost Access. ACS Synth. Biol. (2022) doi:10.1021/acssynbio.1c00342.

Hammerling, M. J., Warfel, K. F. & Jewett, M. C. Lyophilization of premixed COVID-19 diagnostic RT-qPCR reactions enables stable long-term storage at elevated temperature. Biotechnology Journal vol. 16 2000572 (2021).

Hershewe, J. M.; Warfel, K. F.; Iyer, S. M.; Peruzzi, J. A.; Sullivan, C. J.; Roth, E. W.; DeLisa, M. P.; Kamat, N. P.; Jewett, M. C. Improving Cell-Free Glycoprotein Synthesis by Characterizing and Enriching Native Membrane Vesicles. Nat. Commun. 2021, 12 (1). https://doi.org/10.1038/s41467-021-22329-3.

Hunt, A. C., Vögeli, B., Kightlinger, W. K. & Yoesep, D. J. A high-throughput, automated, cell-free expression and screening platform for antibody discovery. bioRxiv (2021).

Hunt, J. P., Yang, S. O., Wilding, K. M. & Bundy, B. C. The growing impact of lyophilized cell-free protein expression systems. Bioengineered 8, 325-330 (2017).

Jaroentomeechai, T .; Stark, J. C.; Natarajan, A.; Glasscock, C. J.; Yates, L. E.; Hsu, K. J.; Mrksich, M.; Jewett, M. C.; Delisa, M. P. Single-Pot Glycoprotein Biosynthesis Using a Cell-Free Transcription-Translation System Enriched with Glycosylation Machinery. https://doi.org/10.1038/s41467-018-05110-x.

Wang, Y. & Zhang, Y.-H. P. Cell-free protein synthesis energized by slowly-metabolized maltodextrin. BMC Biotechnol. 9, 58 (2009).

Jung, J. K. et al. Cell-free biosensors for rapid detection of water contaminants. Nat. Biotechnol. 38, 1451-1459 (2020).

Karig, D. K .; Bessling, S.; Thielen, P.; Zhang, S.; Wolfe, J. Preservation of Protein Expression Systems at Elevated Temperatures for Portable Therapeutic Production. J. R. Soc. Interface 2017, 14 (129). https://doi.org/10.1098/rsif.2016.1039.

Karim, A. S. et al. In vitro prototyping and rapid optimization of biosynthetic enzymes for cell design. Nat. Chem. Biol. 16, 912-919 (2020).

Khalil, I. et al. Enterotoxigenic *Escherichia coli* (ETEC) vaccines: Priority activities to enable product development, licensure, and global access. Vaccine 39, 4266-4277 (2021).

Kim, D.-M. & Swartz, J. R. Efficient production of a bioactive, multiple disulfide-bonded protein using modified extracts of *Escherichia coli*. Biotechnol. Bioeng. 85, 122-129 (2004).

Kim, H. C.; Kim, T. W.; Kim, D. M. Prolonged Production of Proteins in a Cell-Free Protein Synthesis System Using Polymeric Carbohydrates as an Energy Source. Process Biochem. 2011. https://doi.org/10.1016/j.procbio.2011.03.008.

Kim, T.-W. et al. An economical and highly productive cell-free protein synthesis system utilizing fructose-1,6-bisphosphate as an energy source. Journal of Biotechnology vol. 130 389-393 (2007).

Lee, C. H. & Tsai, C. M. Quantification of bacterial lipopolysaccharides by the purpald assay: measuring formaldehyde generated from 2-keto-3-deoxyoctonate and heptose at the inner core by periodate oxidation. Anal. Biochem. 267, 161-168 (1999).

Liu, X. et al. Design of a Transcriptional Biosensor for the Portable, On-Demand Detection of Cyanuric Acid. ACS Synth. Biol. 9, 84-94 (2020).

McNerney, M. P. et al. Point-of-care biomarker quantification enabled by sample-specific calibration. Sci Adv 5, eaax4473 (2019).

Micoli, F., Costantino, P. & Adamo, R. Potential targets for next generation antimicrobial glycoconjugate vaccines. FEMS Microbiol. Rev. 42, 388-423 (2018).

Narang, S. A_, Hansen M. Hsiung, and Roland Brousseau. "[6] Improved phosphotriester method for the synthesis of gene fragments." Methods in Enzymology. vol. 68. Academic Press, 1979. 90-98.

Owczarzy, Richard, et al. "Predicting stability of DNA duplexes in solutions containing magnesium and monovalent cations." Biochemistry 47.19 (2008): 5336-5353.

Pardee, K. et al. Rapid, Low-Cost Detection of Zika Virus Using Programmable Biomolecular Components. Cell 165, 1255-1266 (2016).

Pardee, K.; Slomovic, S.; Nguyen, P. Q.; Lee, J. W.; Donghia, N.; Burrill, D.; Ferrante, T.; McSorley, F. R.; Furuta, Y.; Vernet, A.; et al. Portable, On-Demand Biomolecular Manufacturing. Cell 2016, 167 (1), 248-259.e12. https://doi.org/10.1016/j.cell.2016.09.013.

(56) References Cited

OTHER PUBLICATIONS

Wetmur, James G. "DNA probes: applications of the principles of nucleic acid hybridization." Critical reviews in biochemistry and molecular biology 26.3-4 (1991): 227-259.

Rappuoli, R., De Gregorio, E. & Costantino, P. On the mechanisms of conjugate vaccines. Proceedings of the National Academy of Sciences of the United States of America vol. 116 14-16 (2019).

Rasor, B. J., Yi, X., Brown, H., Alper, H. S. & Jewett, M. C. An integrated in vivo/in vitro framework to enhance cell-free biosynthesis with metabolically rewired yeast extracts. Nat. Commun. 12, 5139 (2021).

Salehi, A. S. M. et al. Cell-free protein synthesis of a cytotoxic cancer therapeutic: Onconase production and a just-add-water cell-free system. Biotechnol. J. 11, 274-281 (2016).

Stark, J. C. et al. BioBitsTM Bright: A fluorescent synthetic biology education kit. Sci Adv 4, eaat5107 (2018).

Silverman, A. D., Karim, A. S. & Jewett, M. C. Cell-free gene expression: an expanded repertoire of applications. Nat. Rev. Genet. 21, 151-170 (2020).

Smith, M. T., Berkheimer, S. D., Werner, C. J. & Bundy, B. C. Lyophilized *Escherichia coli*-based cell-free systems for robust, high-density, long-term storage. Biotechniques 56, 186-193 (2014).

Stark, J. C.; Jaroentomeechai, T.; Moeller, T. D.; Hershewe, J. M.; Warfel, K. F.; Moricz, B. S.; Martini, A. M.; Dubner, R. S.; Hsu, K. J.; Stevenson, T. C.; et al. On-Demand Biomanufacturing of Protective Conjugate Vaccines. Sci. Adv. 2021, 7 (6), eabe9444. https://doi.org/10.1126/sciadv.abe9444.

Wilding, K. M.; Zhao, E. L.; Earl, C. C.; Bundy, B. C. Thermostable Lyoprotectant- Enhanced Cell-Free Protein Synthesis for on-Demand Endotoxin-Free Therapeutic Production. N. Biotechnol. 2019, 53, 73-80. https://doi.org/10.1016/J.NBT.2019.07.004.

Yang, J., Cui, Y., Cao, Z., Ma, S. & Lu, Y. Strategy exploration for developing robust lyophilized cell-free systems. Biotechnology Notes 2, 44-50 (2021).

Zawada, J. F. et al. Microscale to manufacturing scale-up of cell-free cytokine production—a new approach for shortening protein production development timelines. Biotechnol. Bioeng. 108, 1570-1578 (2011).

Gabrielli et al. Translation of Histone Messenger RNA by Homologous Cell-Free Systems from Synchronized Hela Cells, Eur J Biochem, 1974, vol. 42, pp. 121-128.

Warfel et al. A low-cost, thermostable, cell-free protein synthesis platform for on demand production of conjugate vaccines, bioRXiv, Aug. 12, 2022, https://doi.org/10.1101/2022.08.10.503507, pp. 1-31, [retrieved on Sep. 15, 2022]. Retrieved from the internet: <URL:https://www.biorxiv.org/content/10.1101/2022.08.10.503507v1.full.pdf>.

International Search Report and Written Opinion issued Oct. 25, 2022 for PCT/US2022/074212.

Figure 1A- 1G

A mg/mL
0
10
30
60
100 lyoprotectant

5-µL CFE reactions

PEP = energy source

Lyophilize

Store reactions vaccum sealed bag dessicant cards

Rehydrate

Measure sfGFP yield lyophilized, no storage 1 week 2 week 4 week

Figures 3A, 3B, 3C, 3D, 3E, 3F, 3G:
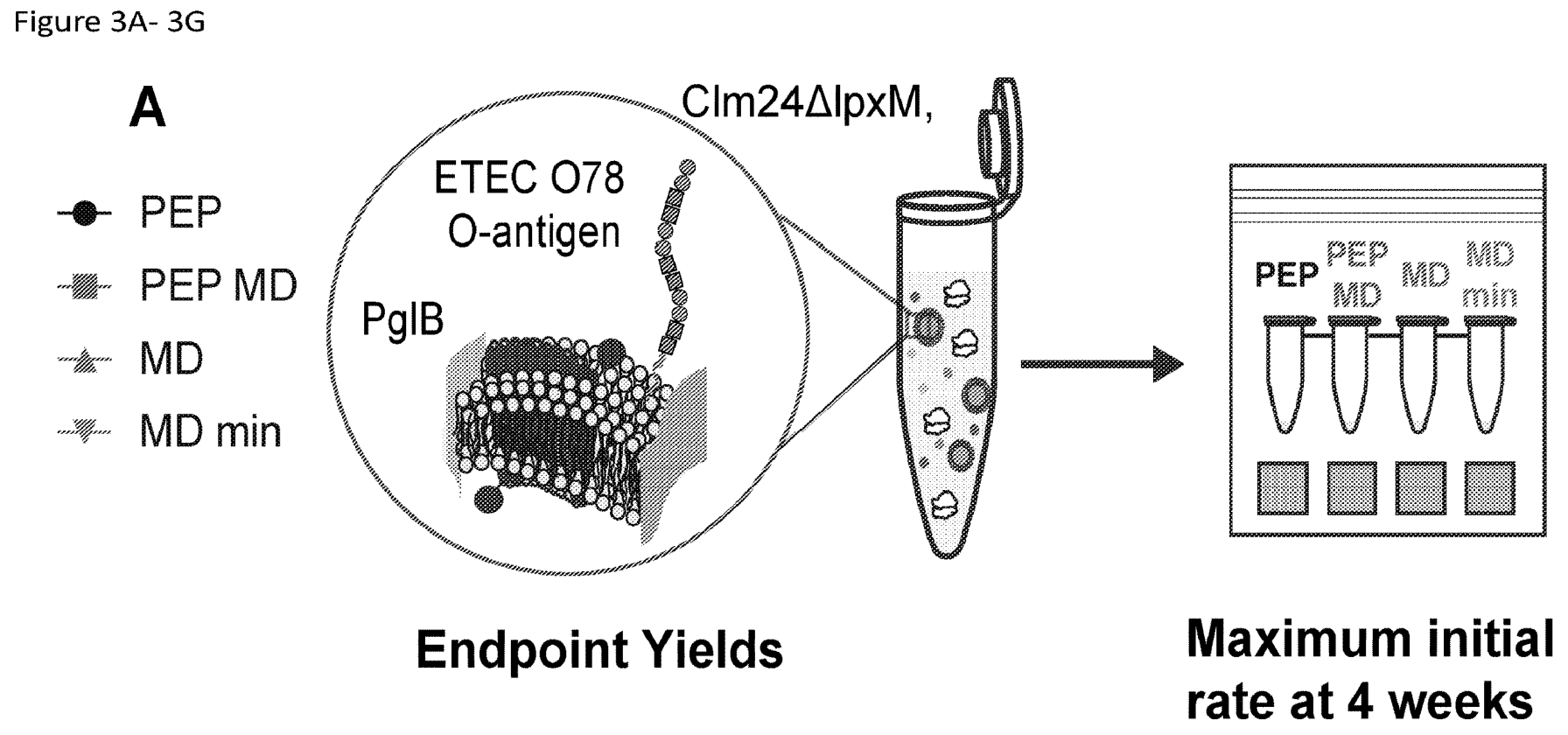

PEP

PEP MD

MD

MD min

ETEC O78
O-antigen

PglB

Clm24ΔlpxM,

Endpoint Yields

PEP

PEP MD

MD

MD min

Maximum initial
rate at 4 weeks

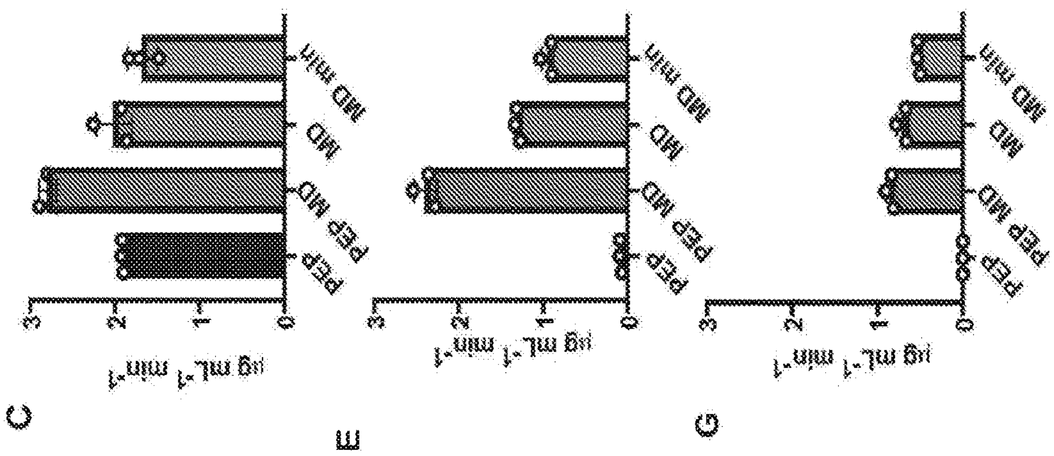
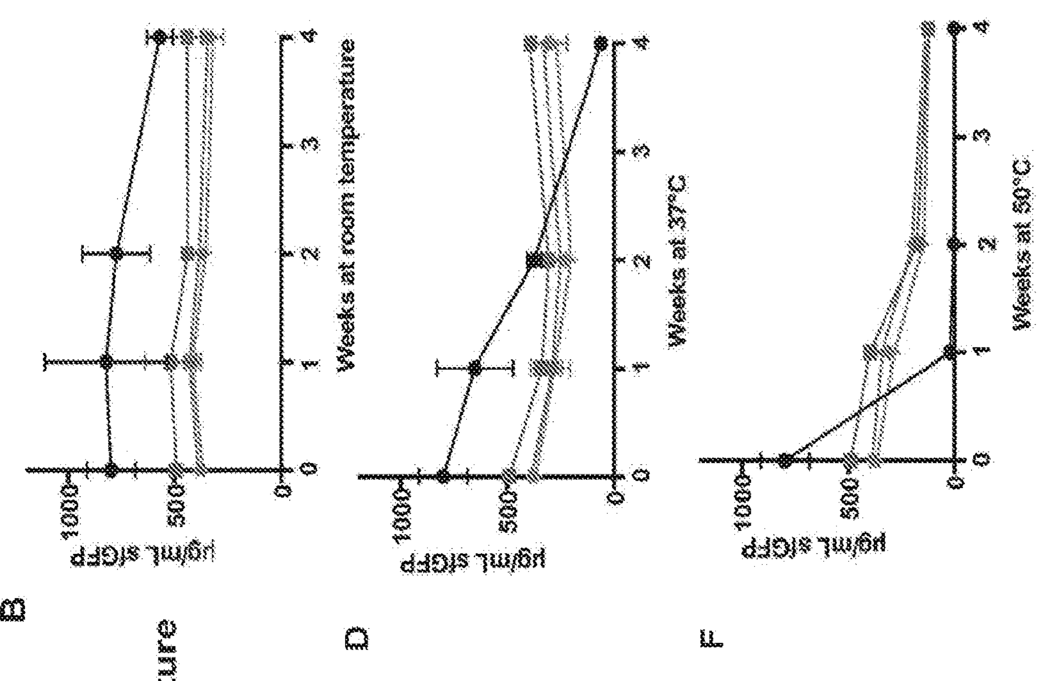
Figure 3A- 3G continued

A
Room Temperature
μg/mL PD
Weeks of Storage at Room Temperature
B
37°C
μg/mL PD
Weeks of Storage at 37°C
C
50°C
μg/mL PD
Weeks of Storage at 50°C
PEP
PEP MD
MD
MD min
D
Storage at 50°C
0 weeks
4 weeks
μg/mL PD-O78
n.d.
E
Weeks at 50°C
no gly
kDa
F
4 weeks of storage
Estimated cost per dose ($)
Storage Temperature
RT
37
50

A
μg/mL sfGFP
1500
1000
500
0
4
6
8
10
12
14
mM Mg
B
μg/mL sfGFP
1500
1000
500
0
0
25
50
75
100
potassium phosphate dibasic (mM)
HEPES pH 7.2
Bis-Tris pH 7.2
Bis-Tris pH 10 (unadjusted)
C
final reaction pH
7.0
6.5
6.0
5.5
0
25
50
75
100
potassium phosphate dibasic (mM)
HEPES pH 7.2
Bis-Tris pH 7.2
Bis-Tris pH 10 (unadjusted)

A
µg/mL sfGFP
1000
800
600
400
200
0
4
6
8
10
12
14
mM Mg
B
µg/mL sfGFP
0
25
50
75
100
potassium phosphate dibasic (mM)
HEPES pH 7.2
Bis-Tris pH 7.2
Bis-Tris pH 10 (unadjusted)
C
final reaction pH
7.0
6.5
6.0
5.5
potassium phosphate dibasic (mM)
HEPES pH 7.2
Bis-Tris pH 7.2
Bis-Tris pH 10 (unadjusted)

A
Maximum initial rates
Fresh
Lyo
μg mL-1 min-1
4
3
2
1
0
PEP
PEP MD
MD
MD min
Formulation
1 week
2 weeks
4 weeks
Room temperature
RT
37°C
50°C PEP
PEP MD
MD
MD min
Fresh and Lyophilized Controls
1 week
2 weeks
4 weeks
RFU
60000
40000
20000
0
Time (min)
0
100
200
300

A

B

A
kDa
PEP
PEP MD
MD
MD min
L
F
L
-
+
+
260-
125-
70-
PD-4xDQNAT (42 kDa)-
38-
25-
αHis
B
kDa
125-
70-
*
αETECO78

LOW-COST, THERMOSTABLE, LYOPHILIZED, CELL-FREE PROTEIN SYNTHESIS PLATFORM

CROSS-REFERENCE TO RELATED APPLICATIONS

The present application is a national stage application filed under 35 U.S.C. § 371 of International Application No. PCT/US2022/074212, filed Jul. 27, 2022, which claims priority to U.S. Provisional Patent Application 63/203,709, filed Jul. 28, 2021, and 63/241,799, filed Sep. 8, 2021. Each of the above-referenced patent documents is incorporated herein by reference in its entirety.

STATEMENT REGARDING FEDERALLY SPONSORED RESEARCH OR DEVELOPMENT

This invention was made with government support under CBET-1936789 awarded by the National Science Foundation. The government has certain rights in the invention.

FIELD

The present technology relates to cell-free systems, methods, and kits for bio-manufacturing a desired product, such as a protein, from readily available and inexpensive components. Particularly disclosed herein are systems, methods, and kits providing a thermostable, low-cost, lyophilized, cell-free protein synthesis platform.

BACKGROUND

Maintaining cold-chain conditions is costly and limits distribution to resource-rich locations, but is required by most vaccines and therapeutics. Cell-free reactions can be lyophilized, but these reactions are often not stable after storage above ambient temperature, conditions that could be encountered during shipping and distribution.

SUMMARY

The present disclosure relates to methods, systems, kits, and compositions comprising a cell-free protein synthesis reaction formulation that has increased thermostability in the lyophilized form, and costs less than a typical reaction formulation. The present technology can be used to fill an unmet need by providing a low-cost manufacturing platform that is stable outside of the cold chain to distribute and manufacture proteins, for example, conjugate vaccines.

Cell-free reaction formulations are provided herein that reduce reaction cost, and when lyophilized, are more resilient to high temperature storage. By way of example, these formulations were applied to cell-free reactions using extracts made from *E. coli* BL21DE3* and Clm24 delta IpxM, a strain with remodeled lipid A, and used to produce glycoconjugate vaccines.

In some embodiments, the formulations comprise maltodextrin, as both an energy source and lyoprotectant. In some embodiments, the formulation does not include added phosphorylated energy substrates, or includes a lower amount of a phosphorylated energy substrate than formulations prepared without maltodextrin. In some embodiments, the formulation does not include phosphoenolpyruvic acid (PEP).

Disclosed herein are cell-free protein synthesis (CFPS) reaction composition comprising: a cell lysate; maltodextrin at a concentration of 30-200 mg/mL; and optionally, one or more of: HEPES, phosphate, and Bis-Tris. In some embodiments, the composition does not comprise an additional phosphorylated energy source such as phosphoenolpyruvic acid (PEP). In some embodiments, the composition does not comprise added coenzyme A (CoA), transfer RNA (tRNA) or nucleotide triphosphates (NTPs), and in some embodiments, the composition comprises added nucleotide monophosphates (NMPs).

In some embodiments, CFPS reaction compositions comprise a cell lysate; maltodextrin at a concentration of 10-500 mg/mL; optionally, one or more of: HEPES, phosphate, and Bis-Tris; and an additional phosphorylated energy source such as PEP.

In some embodiments, any of the above-described CFPS reaction compositions comprise one or more of a transcription template and a translation template.

In some embodiments, any of the above-described CFPS reaction compositions comprise a bacterial cell lysate. In some embodiments, the bacterial cell lysate comprises an *E. coli* cell lysate. In some embodiments, the *E. coli* cell lysate comprises BL21DE3* cell lysate. In some embodiments, the cells comprise the Clm24 delta IpxM strain, comprising a remodeled lipid A.

In some embodiments, any of the above-described CFPS reaction compositions comprise about 60 mg/mL maltodextrin; HEPES 7.2; about 75 mM phosphate; about 10 mM Mg; and NMPs; and the composition does not comprise added NTP, tRNA, CoA, and phosphorylated energy sources.

In some embodiments, any of the above-described CFPS reaction compositions is lyophilized. In some embodiments, the lyophilized composition can be stored and/or transported at a temperature between room temperature and about 50° C. for up to four weeks and maintain protein synthesis activity upon rehydration. In some embodiments, the protein synthesis activity is better than a control CFPS reaction composition that does not include maltodextrin.

Disclosed herein are kits comprising any one of the CFPS reaction compositions as described above. In some embodiments, the kits comprise a polymerase. In some embodiments, the polymerase is provided as a glycerol-free composition. In some embodiments, the polymerase is provided as a cell lysate or cell extract. In some embodiments, the kit comprises a positive control nucleic acid template. In some embodiments, the kit can be stored and/or transported at a temperature between room temperature and about 50° C. for up to four weeks and maintain protein synthesis activity upon rehydration. In some embodiments, the protein synthesis activity is better than a control CFPS reaction composition/kit that does not include maltodextrin.

BRIEF DESCRIPTION OF THE DRAWINGS

FIG. 3A-3G. Low-cost formulations preserve CFE reactions with iVAX extract when stored at up to 50° C. (A) Schematic of CFE reaction storage conditions. After four weeks of storage at room temperature (B-C), 37° C. (D-E), and 50° C. (F-G), lyophilized CFE reactions were rehydrated with 5 μL of water and incubated at 30° C. for 20 hours and endpoint sfGFP yields and maximum initial protein synthesis rates were measured. Error bars represent standard deviation of 3 CFE reactions.

DETAILED DESCRIPTION

Figures 1A, 1B, 1C, 1D, 1E, 1F, 1G:
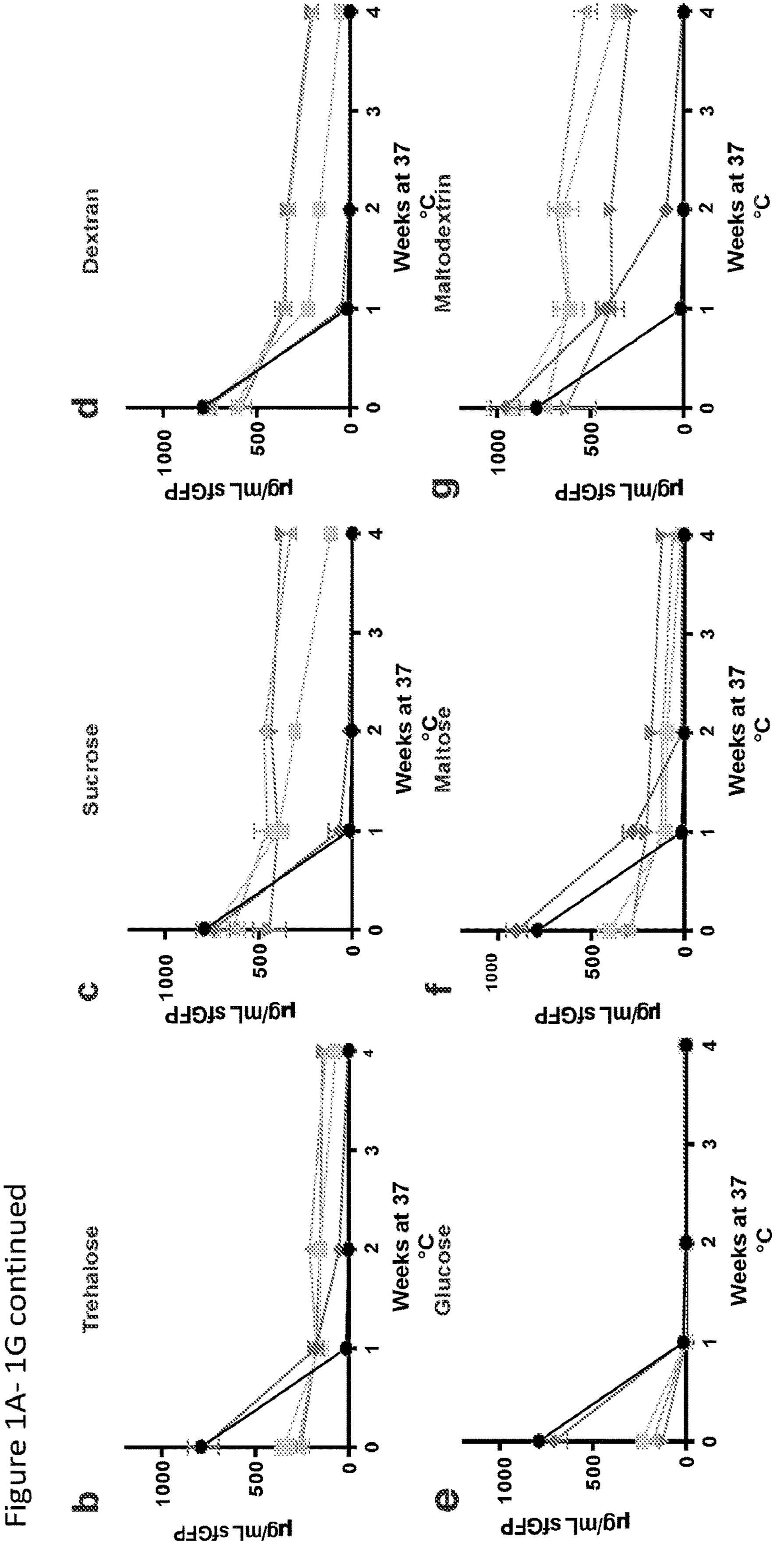
FIG. 1A-IG. Maltodextrin enhances stability of cell-free protein synthesis reactions stored at 37° C. (A) Schematic of CFE reaction set-up and lyophilization for the screening of lyoprotectants. The impact on sfGFP production of (B) trehalose, (C) sucrose, (D) dextran, (E) glucose, (F) maltose, and (G) maltodextrin at concentrations of 0 mg/mL in black circles, 10 mg/mL in blue diamonds, 30 mg/mL in light blue squares, 60 mg/mL in purple triangles, and 100 mg/mL in inverted red triangles on lyophilized CFE reactions after storage was measured. Reactions were rehydrated with 5 μL of water and incubated at 30° C. for 20 hours after one, two, and four weeks of storage at 37° C. Error bars represent standard deviation of 3 CFE reactions.

Cell-free protein production systems can be freeze-dried and used for decentralized small-scale manufacturing at the point-of-care, enabling access and distribution of products, namely conjugate vaccines. However, freeze-dried cell-free conjugate vaccine synthesis reactions have not yet been evaluated for stability above ambient temperature, and vaccine cost is still limiting for low-resource settings. Disclosed herein are methods and compositions that decrease the cost and increase the stability of the freeze-dried cell-free protein synthesis reactions when stored at temperatures up to 50° C. The compositions include lyoprotectants that can increase the stability of freeze-dried reactions and that also act as high-yielding energy substrates, replacing one of the most expensive cell-free protein synthesis reagents: phosphorylated energy substrates.

Reaction formulations were optimized to further drive down the cost while still maintaining protein synthesis activity necessary for producing vaccine doses after storage at temperatures up to 50° C. These improvements were then applied to synthesize exemplary conjugate vaccines for preventing bacterial infections common in resource-limited settings. Overall, this work will enable the synthesis of low-cost, thermostable conjugate vaccines that are both pertinent and accessible.

Definitions

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target", "target sequence", "target region", and "target nucleic acid", as used herein, are synonymous and refer to a region or sequence of a nucleic acid which is to be amplified, sequenced or detected.

The term "hybridization", as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product, typically produced by transcription from an expression template, that can be used by ribosomes to synthesize polypeptide or protein.

The term "reaction mixture" or "reaction composition" as used herein, refers to a solution containing reagents necessary to carry out a given reaction. A reaction mixture is referred to as complete if it contains all reagents necessary to enable the reaction, and incomplete if it contains only a subset of the necessary reagents. Components for a reaction mixture may be stored separately in separate container, each containing one or more of the total components. Components may be packaged separately for commercialization and useful commercial kits may contain one or more of the reaction components for a reaction mixture.

An "amplification reaction mixture", which refers to a solution containing reagents necessary to carry out an amplification reaction, typically contains oligonucleotide primers and a DNA polymerase in a suitable buffer.

A "PCR reaction mixture", which refers to a solution containing the reagents necessary to carry out a PCR reaction, typically contains DNA polymerase, dNTPs, and a divalent metal cation in a suitable buffer.

A "cell-free protein synthesis (CFPS) reaction mixture", or a "CFPS reaction composition" which refers to a solution containing the reagents necessary to carry out CFPS, typically contains a crude or partially-purified bacterial or yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. By way of example, an RNA translation template may be encoded on a vector. In these and other aspects, the CFPS reaction mixture can also include a DNA-dependent RNA polymerase to direct transcription of an RNA translation template encoding the open reading frame. In these and other aspects, additional NTP's and divalent cation cofactor can be included in the CFPS reaction mixture.

In some embodiments, the CFPS reaction mixture includes a polymerase. The polymerase may be endogenous to the lysate, or the polymerase may be exogenous, and may be added, either as a purified polymerase or as part of a different lysate. By way of example, but not by way of limitation, in some embodiments, a polymerase, such as T7 polymerase, is added to the CFPS reaction mixture (exogenous). In some embodiments, a CFPS reaction mixture comprises one or more lyoprotectants, and in some embodiments, the CFPS reaction mixture is lyophilized, e.g., for long term storage. In some embodiments, the polymerase is provided as a glycerol-free composition.

By way of example but not by way of limitation, in some embodiments, a CFPS reaction mixture comprises a lysate, e.g., a bacterial lysate, one or more lyoprotectants, and a buffer comprising, for example, HEPES, phosphate, Bis-Tris 10, and magnesium. In some embodiments, the RNA translation template is also present in the CFPS reaction mixture, and can be endogenous to the lysate or can be an added component. In some embodiments, the CFPS reaction mixture is lyophilized.

In some embodiments, the CFPS reaction mixture comprises a crude lysate, and does not comprise any additional phosphorylated energy substrate, such as PEP (i.e., no additional phosphorylated energy substrate is added to the reaction). In some embodiments, the only added energy source is also a lyoprotectant, e.g., maltodextrin. In some embodiments, a non-phosphorylated energy substrate is added to the CFPS reaction, in addition to the lyoprotectant, e.g., maltodextran. In other embodiments, a phosphorylated energy substrate is added to the CFPS reaction, in addition to the lyoprotectant, e.g., maltodextran.

A "secondary reaction mixture," which refers to a solution containing the reagents necessary to carry out an enzymemediated biosynthetic steps, typically includes a feedstock that reacts in the presence of the enzyme to produce a final or intermediate product in the metabolic or biosynthetic pathway of interest. A secondary reaction mixture may optionally contain a cofactor, e.g. coenzyme-A, NAD, ATP, or a buffer.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif (1990).

Oligonucleotides and polynucleotides may optionally include one or more non-standard nucleotide(s), nucleotide analog(s) and/or modified nucleotides. Examples of modified nucleotides include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Peptides, Polypeptides, Proteins, and Synthesis Methods

As described herein, the present compositions, kits, and methods are useful to produce proteins. As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 21ufa21hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

It is understood that natural and/or non-natural amino acids may be added to a CFPS reaction mixture for which components (e.g., nucleic acid templates, ribosomes, etc.) are provided to produce proteins comprising any of the natural or non-natural amino acids.

As used herein, a "peptide" is defined as a short polymer of amino acids, of a length typically of 20 or less amino acids, and more typically of a length of 12 or less amino acids (Garrett & Grisham, Biochemistry, 2nd edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length>100 amino acids (Garrett & Grisham, Biochemistry, 2nd edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

A modified amino acid sequence that is disclosed herein may include a deletion in one or more amino acids. As utilized herein, a "deletion" means the removal of one or more amino acids relative to the native amino acid sequence. The modified amino acid sequences that are disclosed herein may include an insertion of one or more amino acids. As utilized herein, an "insertion" means the addition of one or more amino acids to a native amino acid sequence. The modified amino acid sequences that are disclosed herein may include a substitution of one or more amino acids. As utilized herein, a "substitution" means replacement of an amino acid of a native amino acid sequence with an amino acid that is not native to the amino acid sequence.

A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

Disclosed proteins, mutants, or variants, described herein may have one or more functional or biological activities exhibited by a reference polypeptide (e.g., one or more functional or biological activities exhibited by wild-type protein). In some embodiments, the activity of the variant or mutant protein may have an activity that is enhanced, as compared to a comparable wild-type or control enzyme, or may have an alternative or a modified activity as compared to a comparable or wild-type or control enzyme.

Cell-Free Protein Synthesis (CFPS)

The components, systems, and methods disclosed herein may be applied to, or adapted to cell-free protein synthesis methods as known in the art. See, for example, U.S. Pat. Nos. 5,478,730; 5,556,769; 5,665,563; 6,168,931; 6,548,276; 6,869,774; 6,994,986; 7,118,883; 7,186,525; 7,189,528; 7,235,382; 7,338,789; 7,387,884; 7,399,610; 7,776,535; 7,817,794; 8,703,471; 8,298,759; 8,715,958; 8,734,856; 8,999,668; and 9,005,920. See also U.S. Published Application Nos. 2018/0016614, 2018/0016612, 2016/0060301, 2015-0259757, 2014/0349353, 2014-0295492, 2014-0255987, 2014-0045267, 2012-0171720, 2008-0138857, 2007-0154983, 2005-0054044, and 2004-0209321. See also U.S. Published Application Nos. 2005-0170452; 2006-0211085; 2006-0234345; 2006-0252672; 2006-0257399; 2006-0286637; 2007-0026485; 2007-0178551. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non-standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098,578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

As described above, in some embodiments, a "CFPS reaction mixture" typically may contain a crude or partially-purified cell extract (e.g., a yeast or bacterial extract), an RNA translation template, and a suitable reaction buffer for promoting cell-free protein synthesis from the RNA translation template. In some embodiments, the CFPS reaction mixture can include exogenous RNA translation template. In some embodiments, the CFPS reaction mixture can include a DNA expression template encoding an open reading frame operably linked to a promoter element for a DNA-dependent RNA polymerase. In some embodiments, the CFPS reaction mixture can also include a DNA-dependent RNA polymerase to direct transcription of an RNA translation template encoding the open reading frame. In some embodiments, additional NTP's and divalent cation cofactor can be included in the CFPS reaction mixture. In some embodiments, the CFPS reaction mixture comprise one or more lyoprotectants, and is lyophilized. A reaction mixture is referred to as complete if it contains all reagents necessary to enable the reaction, and incomplete if it contains only a subset of the necessary reagents. It will be understood by one of ordinary skill in the art that reaction components may routinely be stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components may be packaged separately for commercialization and that useful commercial kits may contain any subset of the reaction components of the invention.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

In some embodiments, CFPS reactions include a crude or partially-purified cell extract. In some embodiments, the cells used to derive the crude or partially purified extract may be selected based on the presence or absence of specific endogenous biochemical pathways, and/or engineered biochemical pathways. For example, cells that direct carbon flux, prevent or minimize side product formation, and prevent or minimize promiscuous background activity may be advantageous as compared to other cells. In some embodiments, the cell is a prokaryotic cell (e.g., bacterial cell) or a eukaryotic cell (e.g., a yeast cell). In some embodiments, the cell is a prokaryotic cell and comprises and *E. coli* cell. In some embodiments, the *E. coli* cell comprises a modified *E. coli* cell, such as BL21, JST07, MB263, MP263sucD, and JCO1. In some embodiments, the *E. coli* cell comprises JST07. In some embodiments, *E. coli* cells comprising BL21DE3 cells are the source of polymerase, such as T7 polymerase. In some embodiments, the cell is a bacterial cell and is modified for low endotoxin expression. By way of example, in some embodiments, the bacterial strain comprise an *E. coli* strain that includes the Clm24ΔIpxM modification (PglB-LpxE is overexpressed, the ETEC O78 biosynthesis pathway overexpressed; remodeled lipid A used to produce glycoconjugate proteins, such as vaccines). This bacterial strain is not grown with glucose.

For example, a CFPS reaction mixture may include a bacterial lysate, an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the reaction mixture may comprise a coupled transcription/translation ("Tx/Tl") system where synthesis of translation template and a sequence defined biopolymer from the same cellular extract.

The CFPS reaction mixture may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract. In some embodiments, the polymerase is added to the CFPS reaction mixture. While T7 polymerase is exemplified herein, any polymerase may be used, so long as compatible promoter sequences have been provided. Such engineering would be routine to the skilled artisan.

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts.

The temperature may be any temperature suitable for CFPS. Temperature may be in the general range from about 10° C. to about 40° C., including intermediate specific ranges within this general range, include from about 15° C. to about 35° C., from about 15° C. to about 30° C., from about 15° C. to about 25° C.. In certain aspects, the reaction temperature can be about 15° C., about 16° C., about 17° C., about 18° C., about 19° C., about 20° C., about 21° C., about 22° C., about 23° C., about 24° C., about 25° C.

The reaction mixture may include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The reaction mixture may include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The reaction mixture may include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The reaction mixture may include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In some aspects, the concentration of inorganic cations can be within the specific range from about 4 mM to about 9 mM and more preferably, within the range from about 5 mM to about 7 mM. In some aspects, the concentration of inorganic cations by be about 8-10 mM.

The reaction mixture may include endogenous NTPs (i.e., NTPs that are present in the cell extract) and/or exogenous NTPs (i.e., NTPs that are added to the reaction mixture). In some embodiments, the reaction uses ATP, GTP, CTP, and UTP. In some embodiments, the concentration of individual NTPs is within the range from about 0.1 mM to about 2 mM. In some embodiments, NTP are replaced with or supplemented with NMPs.

Buffers may be added, for example, to modulate or maintain the pH. Exemplary buffers include one or more of HEPES, Tris-Bis. The pH of the buffers can be adjusted, as is well known in the art. By way of example, in some embodiments, a Bis-Tris buffer of pH 5-10 may be used; in some embodiments, a HEPES buffer of pH 5-10 may be used. In some embodiments, the pH of a Bis-Tris buffer may be between 7-10 (e.g., 7.2). In some embodiments, the pH of a HEPES buffer may be between 7-10 (e.g., 7.2).

In some embodiments, phosphate is provided, for example, between about 0 and 100 mM. In some embodiments, phosphate is provided at between about 25-100 mM, or at about 75 mM.

The reaction mixture may include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, translation, and/or secondary reaction steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In some embodiments, the CFPS reaction mixture includes one or more lyoprotectants. By way of example, but not by way of limitation, lyoprotectants include mono, di, or trisacchsrides, such as but not limited to ribose, sucrose, lactose, raffinose, trehalose, dextran, maltose, and maltodextrin. In some embodiments, the CFPS reaction mixture includes maltodextrin. In some embodiments, the lyoprotectant is provided at about 10-500 mg/mL, at about 10-400 mg/mL, at about 10-300 mg/mL, at about 10-200 mg/mL, at about 10-100 mg/mL, or at about 20, 30, 40, 50, 60, 70 80, or 90 mg/mL. In some embodiments, the lyoprotectant is provided at about 60 mg/mL. In some embodiments, the CFPS reaction mixture includes a lyoprotectant such as maltodextrin and does not include additional phosphorylated energy substrates, such as PEP, or includes a lower amount, or a lower concentration of an added phosphorylated energy substrate than a CPFS reaction mixture that does not include maltodextrin. In some embodiments, the CPFS reaction mixture includes, in addition to a lyoprotectant such as maltodextrin, HEPES 7.2, phosphate, and Mg, and does not include added phosphorylated energy substrates such as PEP. In some embodiments, the CPFS reaction mixture includes, in addition to a lyoprotectant such as maltodextrin, HEPES 7.2, phosphate, and Mg, and does not include added phosphorylated energy substrates such as PEP, and does not include added coenzyme A (CoA), transfer RNA (tRNA), or nucleotide triphosphates (NTPs); in some embodiments, NMPs are provided instead of NTPs. In some embodiments, the CFPS reaction mixtures are lyophilized for storage. In some embodiments, the lyophilized reaction are stored or transported at room temperature or higher, such as 37° C., or at 50° C. In some embodiments, lyophilized CFPS reaction mixtures stored at room temperature or higher, and comprising maltodextrin, HEPES 7.2, phosphate, and Mg, and not including additional phosphorylated energy substrates such as PEP, perform better (e.g., express higher amounts of a target protein), than a CFPS extract lyophilized without maltodextrin, and comprising added phosphorylated energy substrates such as PEP.

As discussed in the section below, the disclosed CFPS compositions, systems, kits, and methods provide several advantages over prior art CFPS compositions. For example, the present CFPS compositions including maltodextrin can be lyophilized, and will maintain protein synthesis activity when stored and/or transported at high temperatures (e.g., room temperature up to 50° C.) for up to four weeks, or longer. The protein synthesis activity is higher than that of a comparable, or control CFPS composition that does not include maltodextrin. As used herein a "control" or "comparable" CFPS composition refers to a composition that includes the same components, and/or that has been prepared and treated in the same way as the "test" composition, except for the selected variable(s), e.g., the presence/absence of maltodextrin, PEP, CoA, etc.

The current compositions need not be refrigerated. In some embodiments, the CFPS reaction compositions and kit comprising the same can be stored and/or transported at a temperature between room temperature and about 50° C. for up to four weeks and maintain protein synthesis activity upon rehydration. In some embodiments, the protein synthesis activity is better than a control CFPS reaction composition/kit, e.g., a composition or a kit that does not include maltodextrin.

In some embodiments, the protein synthesized by the CFPS reactions of the present disclosure is formulated as a vaccine. In some embodiments, the vaccine is prophylactic. In some embodiments, the vaccine is therapeutic. In some embodiments, the protein is isolated, purified, or concentrated from the CFPS reaction composition. In some embodiments, the protein is glycosylated.

Applications and Advantages

The systems, methods, compositions, and components disclosed herein find use in numerous applications and advantages. Non-limiting examples for the thermostable, lyophilized CFPS reaction mixtures include the following:

- On-demand production of proteins without cold-chain transportation.
- On-demand production of glycoconjugate vaccines.
- Low-cost, thermostable, lyophilized cell-free protein synthesis reactions.
- Preserves protein synthesis capabilities of lyophilized cell-free protein synthesis reactions after storage at elevated temperatures up to 50° C.
- Reduces cost of cell-free protein synthesis reactions.
- Generalizable to different strains of *E. coli*, e.g. strains for producing specialized products such as conjugate vaccines.

The present technology increases the thermostability and decreases the cost of a cell-free platform capable of synthesizing conjugate vaccines and other protein products at the point of care.

This will enable distribution of lyophilized reactions capable of synthesizing conjugate vaccines and protein products without cold-chain storage at a lower cost than the current cell-free protein synthesis reactions.

Exemplary Embodiments

Embodiment 1. A composition, or a method using the composition, comprising: cell-free reaction formulation utilizing 30-200 mg/mL with an optimum of 60 mg/mL maltodextrin as both an energy source and a lyoprotectant capable of protecting protein synthesis capabilities for up to 4 weeks at up to 50° C.

Embodiment 2. The composition or method of embodiment 1 where maltodextrin is added to a cell-free protein synthesis reaction to function as a lyoprotectant in addition to a phosphorylated energy substrate PEP to preserve lyophilized reaction activity.

Embodiment 3. The composition or method of embodiment 1 where maltodextrin is added to a cell-free protein synthesis reaction to function as both the energy substrate as well as a lyoprotectant to preserve lyophilized reaction activity. In some embodiments, the composition comprises no added phosphorylated energy source, such as PEP.

Embodiment 4. The composition or method of embodiment 1 where maltodextrin is added to a low-cost cell-free protein synthesis reaction to function as both the energy substrate as well as a lyoprotectant to preserve lyophilized reaction activity.

Embodiment 5. The composition or method of any of the previous embodiments, comprising removal of exogenously added CoA, tRNA.

Embodiment 6. The composition or method of any of the previous embodiments comprising replacement of NTPs with NMPs.

Embodiment 7. The composition or method of any of the previous embodiments where the reaction formulations are used with glycosylation-competent strains (Clm24 or Clm24 delta IpxM) to produce glycoconjugate vaccines.

Embodiment 8. The composition or method of any of the previous embodiments, wherein the cost of manufacturing the composition is reduced, the stability of the composition is increased, and/or wherein the method and/or composition results in reduced the cost and increased stability of cell-free protein synthesis platforms for on-demand manufacturing.

Example

A Low-Cost, Thermostable, Cell-Free Protein Synthesis Platform for On-Demand Production of Glycoconjugate Vaccines Cell-free expression (CFE) systems have been widely adopted in recent years for prototyping[1-4] and biomanufacturing[5,6] of protein products due to their ease-of-use and control over reaction conditions.[7] The linear scalability of CFE from the 1-nL to 100-L scale enables rapid development and protein manufacturing for disease response.[8,9] Further, CFE reactions can be easily lyophilized and reconstituted[10] making them a versatile platform for point-of-care diagnostics[11-14] as well as therapeutic and vaccine production.[5,15,16] Towards this goal, products such as pyocin,[17] nanobodies," a protein-based vaccine (DT),[18] and a cancer therapeutic (ErA) have already been synthesized in lyophilized CFE reactions that have been stored at temperatures above ambient distribution conditions.[19] A recently developed lyophilized glycoconjugate vaccine synthesis platform (iVAX)[5,20] would have great impact[21,24] if manufactured in a low-cost, thermostable system. However, CFE reactions are expensive, on the order of ~$5.00 per reaction, making them infeasible for distribution and use in resource-limited settings. Adjusting CFE reaction formulations to improve the cost and stability of lyophilized reactions could address this challenge.

Formulation optimization studies have primarily focused on replacing and reducing the most expensive reagents in CFE reactions. Specifically, phosphorylated energy sources (e.g., phosphoenol pyruvate) account for a large portion of reaction cost[7] and have thus served as the first target for optimization. Glucose,[25-27] maltose,[28,29] maltodextrin[28-31], and soluble starch[32] are all low cost alternatives that have been used as energy sources in CFE systems. The necessity of other reagents including nucleotides and cofactors has also been evaluated in the context of formulations to achieve a lower cost reaction.[25,33,34]

Optimizations have also been performed to improve CFE reaction stability after storage. For instance, lyophilized reactions retain activity after ambient storage,[10] but lyoprotectant additives, including the disaccharides trehalose and sucrose, or the oligosaccharide dextran,[17,19,35] have improved stability of lyophilized CFE reactions, especially when stored at high temperatures. Sugars stabilize proteins in lyophilized formulations through mechanisms such as water replacement or vitrication,[36] and have been used in purified protein and in vitro reconstituted systems.[37-39] In addition, lysate-based CFE reactions have been demonstrated to be stable at elevated storage temperatures with the addition of lyoprotectants or strategic separate storage of components.[17-19] However, to date, optimizations have typically sought to address either cost or thermostability rather than considering both formulation properties together.

In this work, we seek to address both cost and stability of CFE reactions to identify a low-cost and thermostable iVAX formulation to produce glycoconjugate vaccines. First, we screened sugar additives that could potentially serve as both lyoprotectant and energy system. We identified maltodextrin as the best lyoprotectant. We then optimized the formulation to also use maltodextrin as a low-cost energy substrate, reducing the reaction cost to 28% of the original formulation. These formulations are sufficient to protect the cell-free protein synthesis of sfGFP after 4 weeks of storage at room temperature, 37° C., and 50° C. Finally, we demonstrate that cell-free glycoprotein synthesis machinery is still active in all formulations under these storage conditions by producing relevant and effective anti-diarrheal glycoconjugate vaccine molecules (ETEC O78 O-antigen conjugated to the approved carrier PD) using iVAX for <$1.00 per dose under all conditions tested.

Results and Discussion

Maltodextrin Enhances Thermostability of CFE Reactions

On-demand usage and global distribution of CFE technologies requires thermostability. Thus, we wanted to characterize the thermostability of our CFE formulation using a common protein expression lysate derived from BL21 Star (DE3) cells. First, we lyophilized 5-μL reactions containing all reagents for PANOx-SP-based CFE supplemented with DNA encoding sfGFP. Then, after one, two, and four weeks of storage in vacuum sealed bags with desiccant cards, we rehydrated lyophilized reactions with 5 μL of water and measured sfGFP concentrations via fluorescence (FIG. 1A). Rehydrated controls (zero-week timepoint) produced protein comparable to controls that were never lyophilized (fresh) (FIG. 6), but lyophilized CFE reactions with no lyoprotectant additives did not produce sfGFP after 1 week of storage at 37° C. (FIG. 1B; black circles). Lyophilized CFE reactions are not thermostable.

Figure 6:
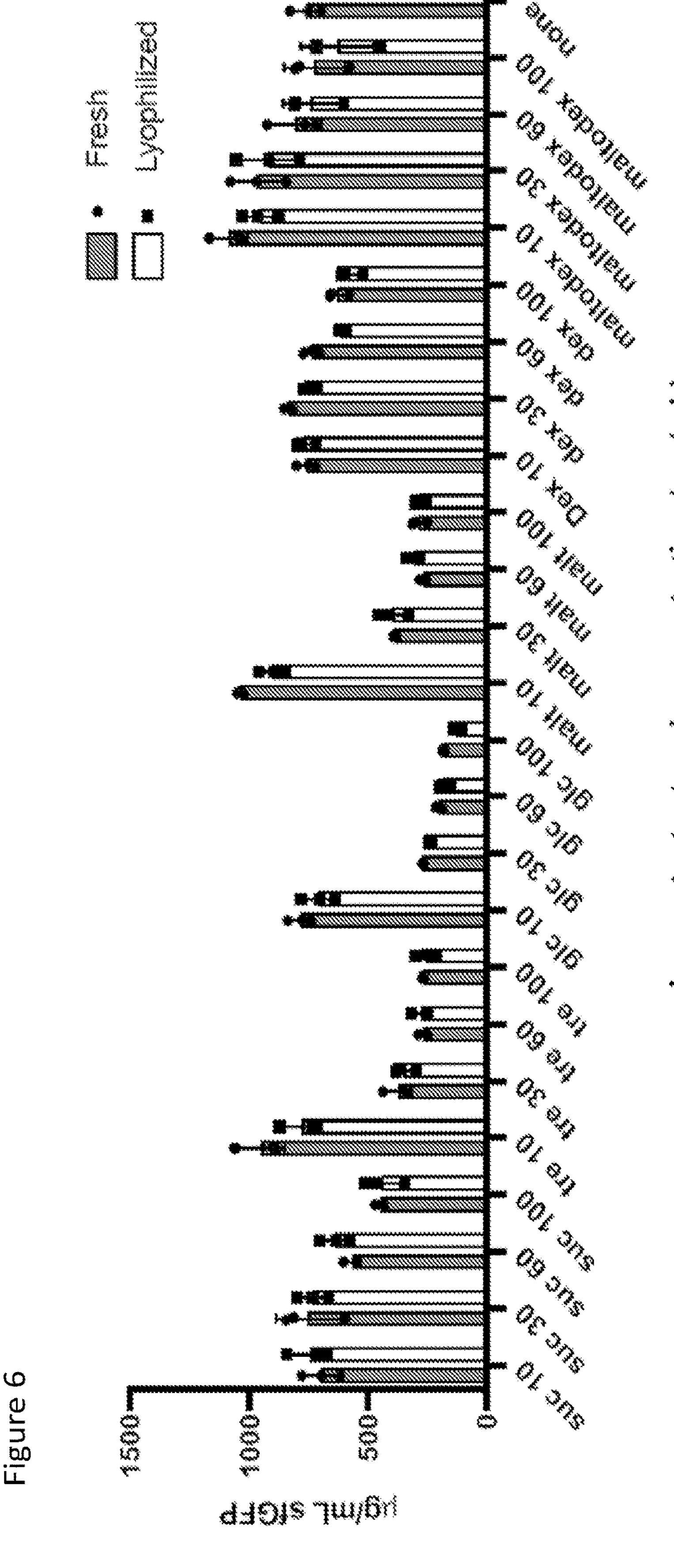
FIG. 6. Impact of lyoprotectant additives on fresh and lyophilized CFE reactions with BL21 Star (DE3) extract. The impact of sucrose (suc), trehalose (tre), glucose (glc), maltose (malt), dextran (dex), and maltodextrin (maltodex) at 0, 10, 30, 60, 100 mg/mL final concentration on fresh (grey bars) and rehydrated lyophilized (white bars) on CFE reaction productivity. Control with no lyoprotectant (none) is shown on the right. Error bars represent standard deviation of 3 CFE reaction replicates (n=3).

We next sought to identify low-cost lyoprotectant additives that could confer storage stability at elevated temperatures (37° C.). Specifically, we explored the use of trehalose,[17] sucrose,[40] and dextran[19] which have previously been shown to enhance lyophilized reaction stability (FIG. 1B-D). In addition, we wanted to test whether sugars that have been demonstrated as energy sources for CFE reactions, such as glucose,[26] maltose,[28,29] and maltodextrin,[28,29,31] could also protect or stabilize reactions during lyophilization and storage (FIGS. 1E-G). To do this we supplemented CFE reactions individually with 0 to 100 mg/mL of each lyoprotectant prior to lyophilization. No significant loss in activity was observed from the lyophilization process, although some lyoprotectants (i.e., trehalose) were detrimental to protein yields (FIG. 6). Then, after one, two, and four weeks of storage, we rehydrated lyophilized reactions with 5 μL of water and measured sfGFP concentrations via fluorescence.

The addition of trehalose, glucose, and maltose each significantly decreased protein expression at concentrations greater than 10 mg/mL in fresh and lyophilized reactions (FIG. 6; FIGS. 1B, E, and F). Supplementing reactions with 100 mg/mL sucrose and dextran retained 85% and 36% of the freshly lyophilized reaction activity (zero-week timepoint) after four weeks of storage, respectively (FIGS. 1C and D). However, adding just 60 mg/mL of maltodextrin retained 71% of the freshly lyophilized reaction activity (zero-week timepoint) and achieved higher overall protein yields after 4 weeks of storage (528+/−61 μg/mL sfGFP) than sucrose-protected reactions (FIG. 1G). Of note, adding maltodextrin protects CFE reactions without any additional costly additives such as DMSO or stabilizers[19] resulting in a simplified and more cost-effective solution.

Maltodextrin can be Used as a Low-Cost CFE Lyoprotectant and Energy Source

Figures 2A, 2B, 2C:
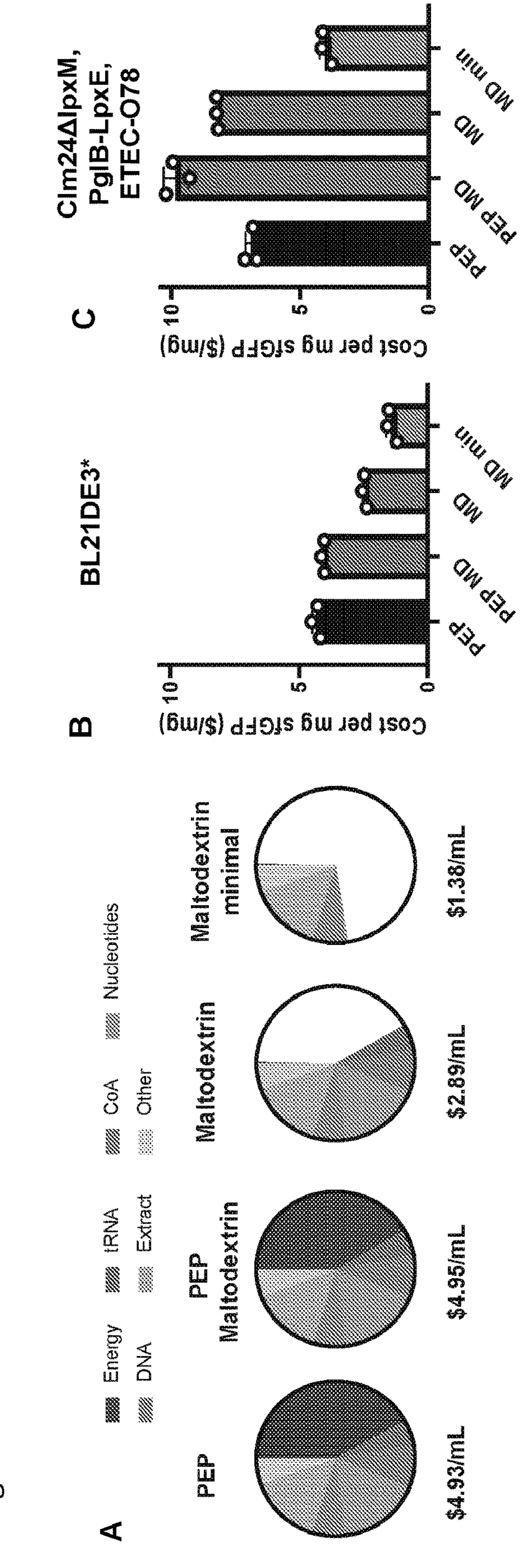
FIG. 2A-2C. Maltodextrin can be effectively used as both an energy source and lyoprotectant for low-cost CFPS. (A) Cost per mL CFE reaction was calculated for each formulation: PEP with no lyoprotectant, PEP with maltodextrin supplemented as a lyoprotectant (PEP MD), maltodextrin as both energy source and lyoprotectant (MD), and maltodextrin without CoA, tRNA, and replacing NTPs with NMPs (MD min). Costs are based upon only raw materials included in the reaction purchased at laboratory scale using calculations in Tables 1-3. (B) Cost per gram sfGFP in CFE reactions using BL21 Star (DE3) extract in all four formulations. (C) Cost per gram sfGFP in CFE reactions using CLM24 ΔIpxM extract in all four formulations. Error bars represent standard deviation of 3 CFE reactions.

After identifying that maltodextrin could be used as an effective lyoprotectant, we wanted to explore whether the polysaccharide could simultaneously act as an energy source for CFE reactions. Maltodextrin, a non-phosphorylated substrate, with the addition of exogenous phosphate, can be broken down into early glycolytic intermediates and used to fuel protein synthesis.[29-31] By having a dual-use for maltodextrin (~$0.02 per mL reaction with 60 mg/mL maltodextrin), we could potentially reduce the cost of a CFE formulation from ~$4.93 per mL reaction to ~$2.89 per mL of reaction (a 59% reduction), by replacing PEP in the PANOx-SP system (Table 1-3; FIG. 2A). Further, replacing nucleotide triphosphates (NTPs) with nucleotide monophosphates (NMPs) which can be phosphorylated in the cell-free reaction and removing non-essential additives like tRNA and CoA[25,33,34] could yield a minimal formulation (MD min) costing ~$1.38 per mL of CFE reaction, a quarter of the cost per mL of the PANOx-SP CFE system.

TABLE 1

Cost breakdown of the CFE reaction formulations used in this work. Cost per liter of CFE reaction for all reagents present in the PEP, PEP MD, MD, and MD min formulation. This table is based on BL21 Star (DE3) extract as is presented in FIG. 2.

| Component | PEP ($/L) | PEP MD ($/L) | MD ($/L) | MD min ($/L) |
|---|---|---|---|---|
| magnesium glutamate | 0.94 | 0.94 | 0.94 | 0.94 |
| ammonium glutamate | 5.97 | 5.97 | 5.97 | 5.97 |
| potassium glutamate | 8.48 | 8.48 | 8.48 | 8.48 |
| ATP | 15.16 | 15.16 | 15.16 | — |
| CTP | 241.05 | 241.05 | 241.05 | — |
| UTP | 277.74 | 277.74 | 277.74 | — |
| GTP | 320.63 | 320.63 | 320.63 | — |
| AMP | — | — | — | 6.91 |
| CMP | — | — | — | 8.86 |
| UMP | — | — | — | 5.85 |
| GMP | — | — | — | 3.70 |
| folinic acid | 22.62 | 22.62 | 22.62 | 22.62 |
| tRNA | 255.00 | 255.00 | 255.00 | — |
| amino acids | 100.54 | 100.54 | 100.54 | 100.54 |
| PEP | 2065.42 | 2065.42 | — | — |
| maltodextrin | — | 19.80 | 19.80 | 19.80 |
| NAD | 110.39 | 110.39 | 110.39 | 110.39 |
| CoA | 435.19 | 435.19 | 435.19 | |
| oxalic acid | 0.19 | 0.19 | 0.19 | 0.19 |
| putrescine | 0.74 | 0.74 | 0.74 | 0.74 |
| spermidine | 5.35 | 5.35 | 5.35 | 5.35 |
| HEPES | 6.06 | 6.06 | — | — |
| Bis-Tris | — | — | 9.77 | 9.77 |
| potassium phosphate dibasic | — | — | 3.18 | 3.18 |
| plasmid DNA | 333.25 | 333.25 | 333.25 | 333.25 |
| extract | 728.25 | 728.25 | 728.25 | 728.25 |
| Total $/L CFE reaction | 4932.97 | 4952.77 | 2894.24 | 1374.79 |
| Total $/mL CFE reaction | 4.93 | 4.95 | 2.89 | 1.37 |

TABLE 2

Cost breakdown of cost of cell extract. Note that the base extract cost is used in all calculations in this work to make claims more generalizable, as variable components are approximately the same for both strains used in this study and are dependent on strain and plasmid used to make extract. Assumptions used in calculations are listed below.

| Compound Name | Vendor | Catalog Number | $/g | $/L culture |
|---|---|---|---|---|
| Constant components | | | | |
| tryptone | Sigma | T7293-1 kg | 0.272 | 4.352 |
| yeast extract | Sigma | Y1625-1 kg | 0.246 | 2.46 |

TABLE 2-continued

Cost breakdown of cost of cell extract. Note that the base extract cost is used in all calculations in this work to make claims more generalizable, as variable components are approximately the same for both strains used in this study and are dependent on strain and plasmid used to make extract. Assumptions used in calculations are listed below.

| | | | | |
|---|---|---|---|---|
| sodium chloride | Sigma | S3014-5 kg | 0.0438 | 0.219 |
| potassium phosphate, monobasic | Sigma | P9791-1 kg | 0.168 | 0.504 |
| potassium phosphate, dibasic | Sigma | 60353-1 kg | 0.312 | 2.184 |
| Variable components | | | | |
| glucose | Sigma | G8270-5 kg | 0.024 | 0.432 |
| IPTG (0.5 mM) | Sigma | 16758-10 g | 49.2 | 5.86218 |
| arabinose (0.02 wt % in media) | Sigma | A3256-1 kg | 1.77 | 0.354 |
| carbenicillin disodium salt | Sigma | C1389-10 g | 70.7 | 7.07 |
| chloramphenicol | Sigma | C0378-100 g | 1.66 | 0.05644 |

| Extract | $/L cells | $/mL extract | $/mL CFE reaction | $/L CFE reaction |
|---|---|---|---|---|
| Base | 9.71 | 2.4275 | 0.72825 | 728.25 |
| BL21 Star (DE3) | 16 | 4 | 1.2 | 1200 |
| iVAX | 17.19 | 4.2975 | 1.28925 | 1289.25 |

Assumptions:

1. 4 mL of extract are produced per liter cell culture.
2. 30% v/v extract is used in CFE reactions.
3. Only raw materials added to cell culture are considered for a base case of extract without variable components such as inducers or antibiotics.
4. Labor costs associated with extract production are not considered.
5. Equipment costs are not considered.

TABLE 3

Information on all reagents added to the CFE reaction. Costs are recorded as of January 2022 at lab scale from vendors used in this work.

| Compound Name | Vendor | Catalog Number | $/g | $/L reaction |
|---|---|---|---|---|
| For PEP formulation | | | | |
| magnesium glutamate (10 mM) | Sigma | 49605-250 g | 0.242 | 0.94 |
| ammonium glutamate | Biosynth | FG28929-.1 kg | 3.6383 | 5.97 |
| potassium glutamate | Sigma | G1501-1 kg | 0.321 | 8.48 |
| ATP | Sigma | A2383-25 G | 22.92 | 15.16 |
| CTP | Sigma | C1506-1 g | 538 | 241.05 |
| UTP | Sigma | U6625-1 g | 594 | 277.74 |
| GTP | Sigma | G8877-1 g | 721 | 320.63 |
| folinic acid | Sigma | 47612-1 g | 754 | 22.62 |
| tRNA | Sigma | 10109550001-.5 g | 1500 | 255.00 |
| amino acids (cost for 1 g of each) | Sigma | LAA21-1kt | 457 | 100.54 |
| PEP | Sigma | 10108294001-1 g | 334 | 2065.42 |
| NAD | Sigma | N8535-15VL | 416 | 110.39 |
| CoA | Sigma | C3144-1 g | 2100 | 435.19 |
| oxalic acid | Sigma | P0963-500 g | 0.26 | 0.19 |
| putrescine | Sigma | P5780-25 g | 4.6 | 0.74 |
| spermidine | Sigma | S2626-25 g | 24.56 | 5.35 |
| HEPES | Sigma | H3375-5 kg | 0.446 | 6.06 |
| Plasmid DNA | Zymo | D4201-50 preps | 25000 | 333.25 |
| For modified formulations | | | | |
| AMP | Sigma | 01930-25 g | 14.72 | 6.91 |
| CMP | Sigma | C1006-5 g | 28.4 | 8.86 |
| UMP | Sigma | U6375-10 g | 18.7 | 5.85 |
| GMP | Sigma | G8377-100 g | 10.7 | 3.70 |
| maltodextrin | Sigma | 419672-500 g | 0.33 | 19.80 |
| Bis-Tris | Sigma | B9754-1 kg | 0.819 | 9.77 |
| potassium phosphate, dibasic | Sigma | 60353-1 kg | 0.312 | 3.18 |
| For iVAX reactions | | | | |
| DDM | Anatrace | D310S-25 g | 39.56 | 39.56 |
| $MnCl_2$ | Sigma | 221279-500 G | 0.272 | 1.35 |

Figures 7A, 7B, 7C:
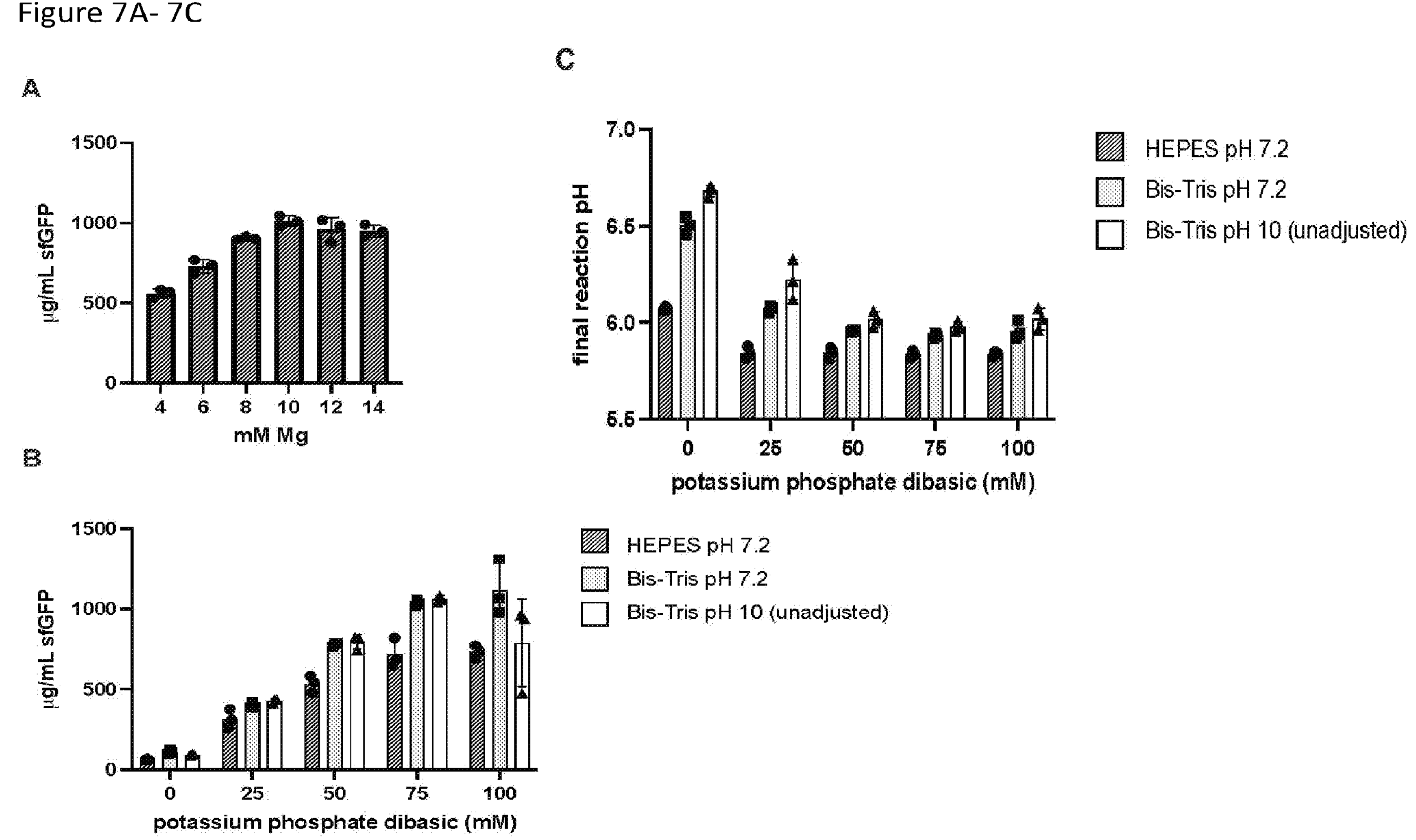
FIG. 7A-7C. Optimization of CFE reagents for MD formulation in BL21 Star (DE3) extract. (A) Magnesium optimization of lysate using PEP as an energy source with sfGFP synthesis as a reporter. (B) Using 10 mM $Mg^{2+}$ in the MD reaction formulation, sfGFP production was used to determine the optimal concentration of potassium phosphate dibasic (pH 7.2) in the CFE reaction. Impact of buffer on the MD formulation was also tested using 57 mM of either HEPES with pH adjusted to 7.2 (dark grey), Bis-Tris with pH adjusted to 7.2 (light grey), or BisTris with unadjusted pH (pH 10) (white). (C) Impact of conditions in B on final pH of the cell-free protein expression measured after 20 hours of sfGFP synthesis at 30° C. Error bars represent standard deviation of 3 CFE reaction replicates (n=3).
Figures 8A, 8B:
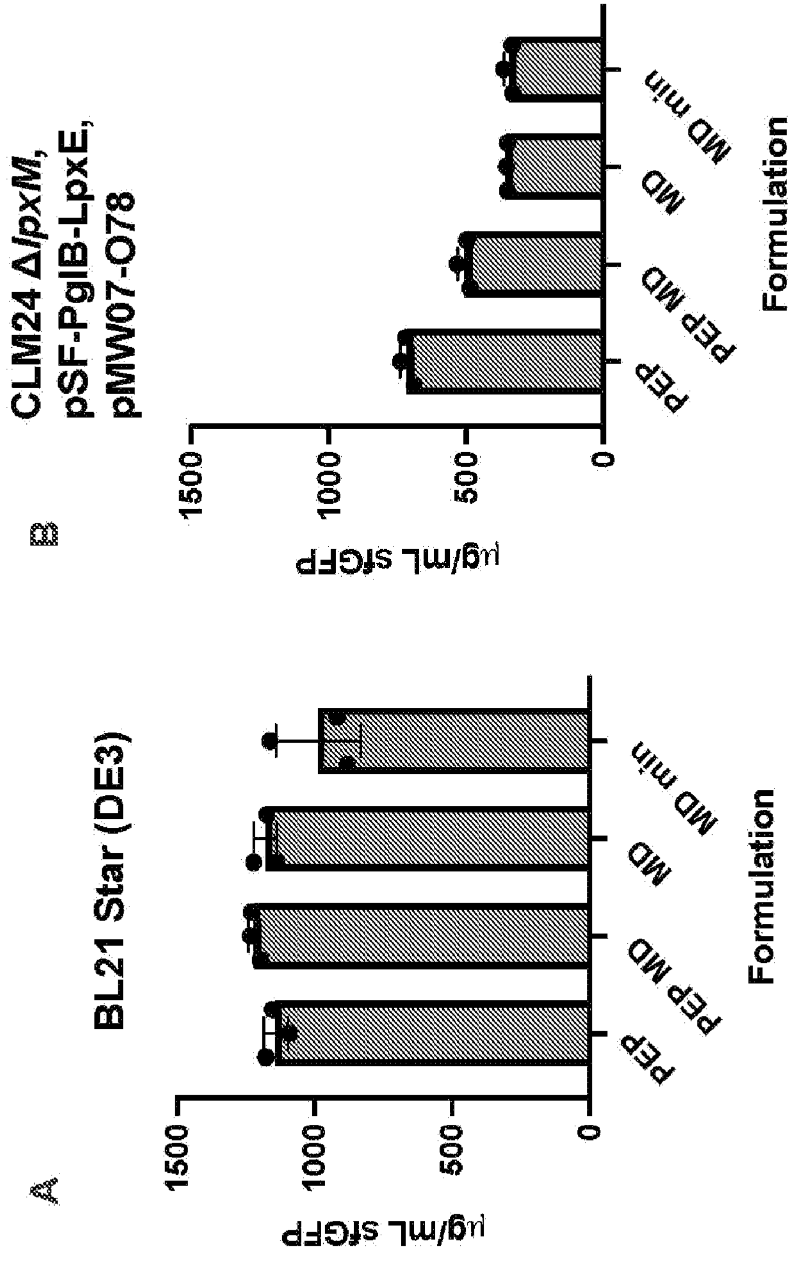
FIG. 8A-8B. sfGFP yields of each formulation in CFE reactions using different extracts. (A) sfGFP synthesis in CFE reactions using BL21 Star (DE3) extract for each formulation. (B) sfGFP synthesis in CFE reactions using the iVAX strain (CLM24 ΔIpxM with overexpression of glycosylation machinery from pSF-PglB-LpxE and pMW07-O78 plasmids) extract for each formulation. Error bars represent standard deviation of 3 CFE reaction replicates (n=3).
Figure 9:
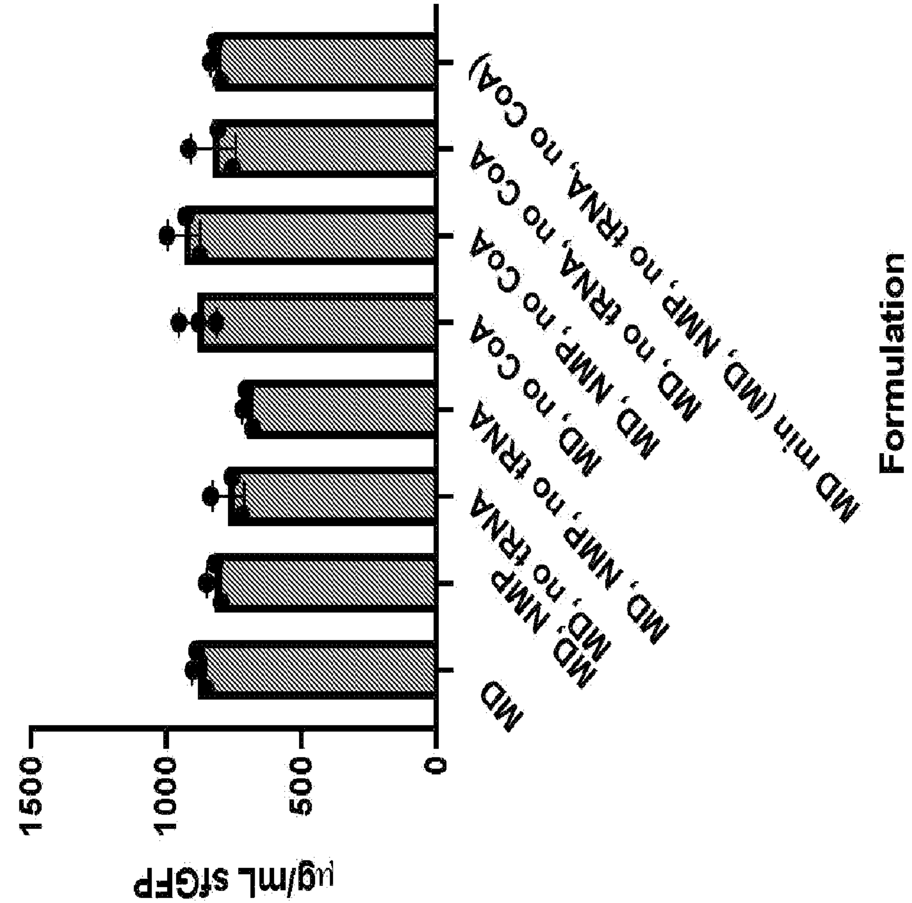
FIG. 9. sfGFP yields in CFE reactions using Bl21 Star (DE3) extract showing the impact of the formulation changes made to the MD formulation to arrive at the MD min formulation. sfGFP yields in a BL21 Star (DE3) extract for the MD formulation (far left) and the impact of changing NTPs to NMPs, removing tRNA, and removing CoA, as well as every combination of the others. sfGFP yields in the MD min formulation (all changes at the same time) are displayed on the far right. Error bars represent standard deviation of 3 CFE reaction replicates (n=3).
Figures 10A, 10B, 10C:
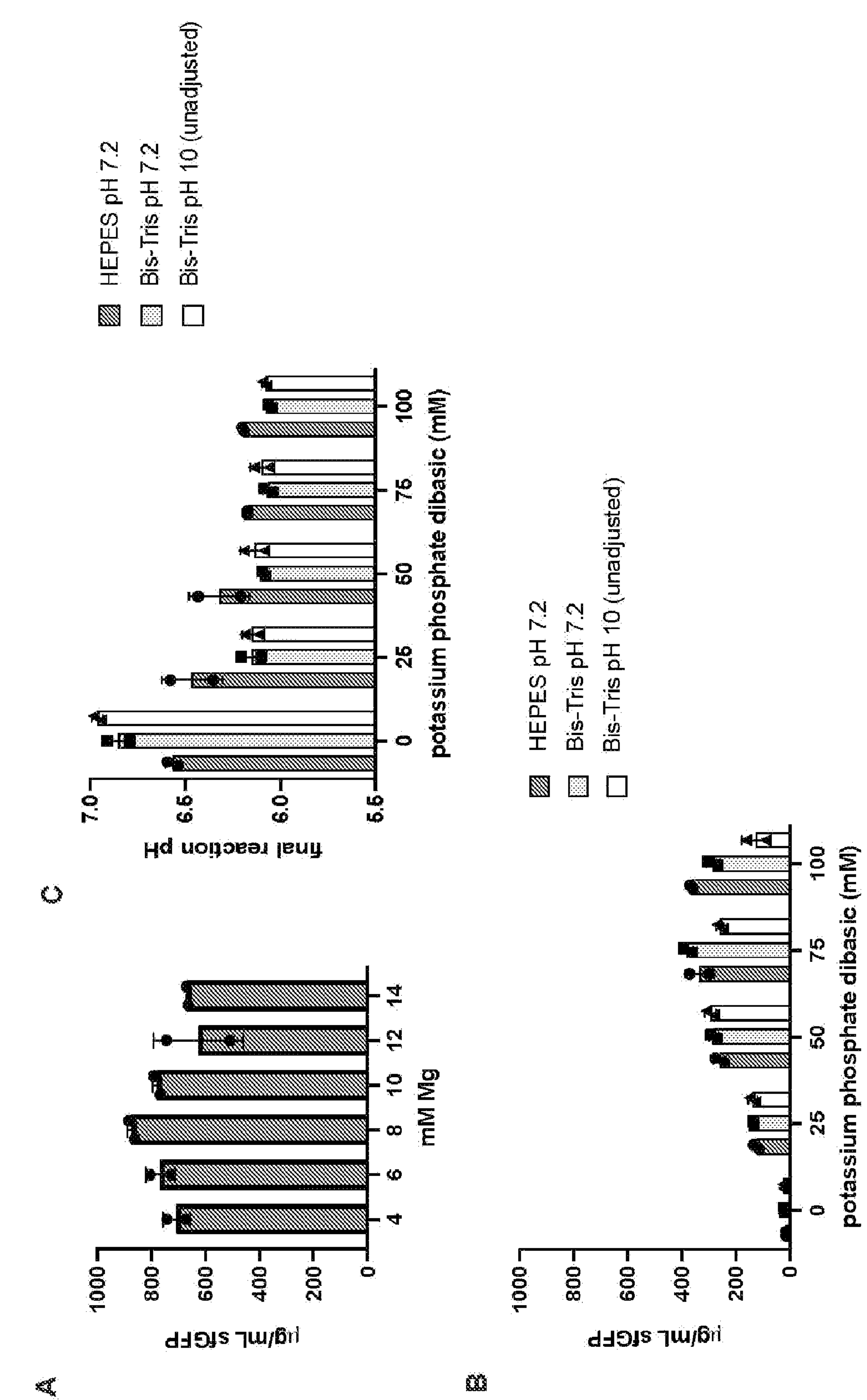
FIG. 10A-10C. Optimization of CFE reagents for MD formulation in iVAX extract (CLM24 ΔIpxM with overexpression of glycosylation machinery from pSF-PglB-LpxE and pMW07-O78 plasmids). (A) Magnesium optimization of lysate using PEP as an energy source and sfGFP synthesis as a readout. (B) Using 8 mM Mg in the MD reaction formulation, sfGFP production was used to determine the optimal concentration of potassium phosphate dibasic (pH 7.2) in the CFE reaction. Impact of buffer on the MD formulation was also tested using 57 mM of either HEPES with pH adjusted to 7.2 (dark grey), Bis-Tris with pH adjusted to 7.2 (light grey), or Bis-Tris with unadjusted pH (pH 10) (white). (C) Impact of conditions in B on final pH of the cell-free reaction measured after 20 hours of sfGFP synthesis at 30° C. Error bars represent average error of 2 CFE reaction replicates (n=2).

To test whether these low-cost maltodextrin formulations could work in practice, we assembled these formulations and evaluated their ability to produce protein. Specifically, we tested four formulations (PEP, PEP+MD, MD, and MD min; Table 4) using extracts from BL21 Star (DE3) and a specialized vaccine production strain (CLM24 ΔIpxM) harboring glycosylation machinery (Table 5)[5] for the synthesis of sfGFP in fresh reactions. We first optimized the addition of exogenous phosphate in the form of potassium phosphate dibasic (75 mM) and buffer (Bis-Tris and HEPES) in maltodextrin-based reactions. For BL21 Star (DE3) extracts, 57 mM Bis-Tris buffer (pH 10) was optimal and maintained higher final reaction pH (FIG. 7).[25,26] Notably, all formulations with these extracts produced roughly the same amount of sfGFP, indicating that the removal of reagents did not impact protein yields (FIG. 8A, 9). Interestingly, the CLM24 ΔIpxM performed better with the HEPES buffer at pH 7.2 (FIG. 10) and 60 mg/mL maltodextrin appeared to have a detrimental impact on sfGFP yields with ~70% protein produced in the PEP MD formulation and ~50% protein produced in both the MD and MD min formulations compared to the original (PEP) formulation (FIG. 8B). Despite this difference, the MD min formulation has a significantly lower cost per milliliter (FIGS. 2B and 2C) and enables protein yields sufficient for glycoconjugate vaccine production (~100 μg/mL),[20] with a maximum yield of ~350 μg/mL sfGFP.

TABLE 4

Components of the CFE reaction formulations used in this work.

| Component | PEP | PEP MD | MD | MD min |
|---|---|---|---|---|
| magnesium glutamate | 10 | 10 | 10 | 10 |
| ammonium glutamate | 10 | 10 | 10 | 10 |
| potassium glutamate | 130 | 130 | 130 | 130 |
| ATP | 1.2 | 1.2 | 1.2 | — |
| CTP | 0.85 | 0.85 | 0.85 | — |
| UTP | 0.85 | 0.85 | 0.85 | — |
| GTP | 0.85 | 0.85 | 0.85 | — |
| AMP | — | — | — | 1.2 |
| CMP | — | — | — | 0.85 |
| UMP | — | — | — | 0.85 |
| GMP | — | — | — | 0.85 |
| folinic acid | 0.03 mg/mL | 0.03 mg/mL | 0.03 mg/mL | |
| tRNA | 0.17 mg/mL | 0.17 mg/mL | 0.17 mg/mL | — |
| amino acids | 2 | 2 | 2 | 2 |
| PEP | 30 | 30 | — | — |
| maltodextrin | — | 60 mg/mL | 60 mg/mL | 60 mg/mL |
| NAD | 0.4 | 0.4 | 0.4 | 0.4 |
| CoA | 0.27 | 0.27 | 0.27 | — |
| oxalic acid | 4 | 4 | 4 | 4 |
| putrescine | 1 | 1 | 1 | 1 |
| spermidine | 1.5 | 1.5 | 1.5 | 1.5 |
| HEPES/Bis-Tris* | 57 | 57 | 57 | 57 |
| potassium phosphate dibasic | — | — | 75 | 75 |
| plasmid DNA | 13.33 ng/μL | 13.33 ng/μL | 13.33 ng/μL | 13.33 ng/μL |
| extract | 30% v/v | 30% v/v | 30% v/v | 30% v/v |

Final concentration present of each reagent used in the CFE reaction for all formulations is provided in mM unless otherwise noted in the table. Cells filled in grey indicate that a component is not present in the reaction formulation described by that column.

*Choice of buffer is extract strain dependent for the MD and MD min formulations, but both buffers were used at the same final concentration.

Low-Cost CFE Formulations Retain Activity when Stored at Up to 50° C.

Figures 11A, 11B:
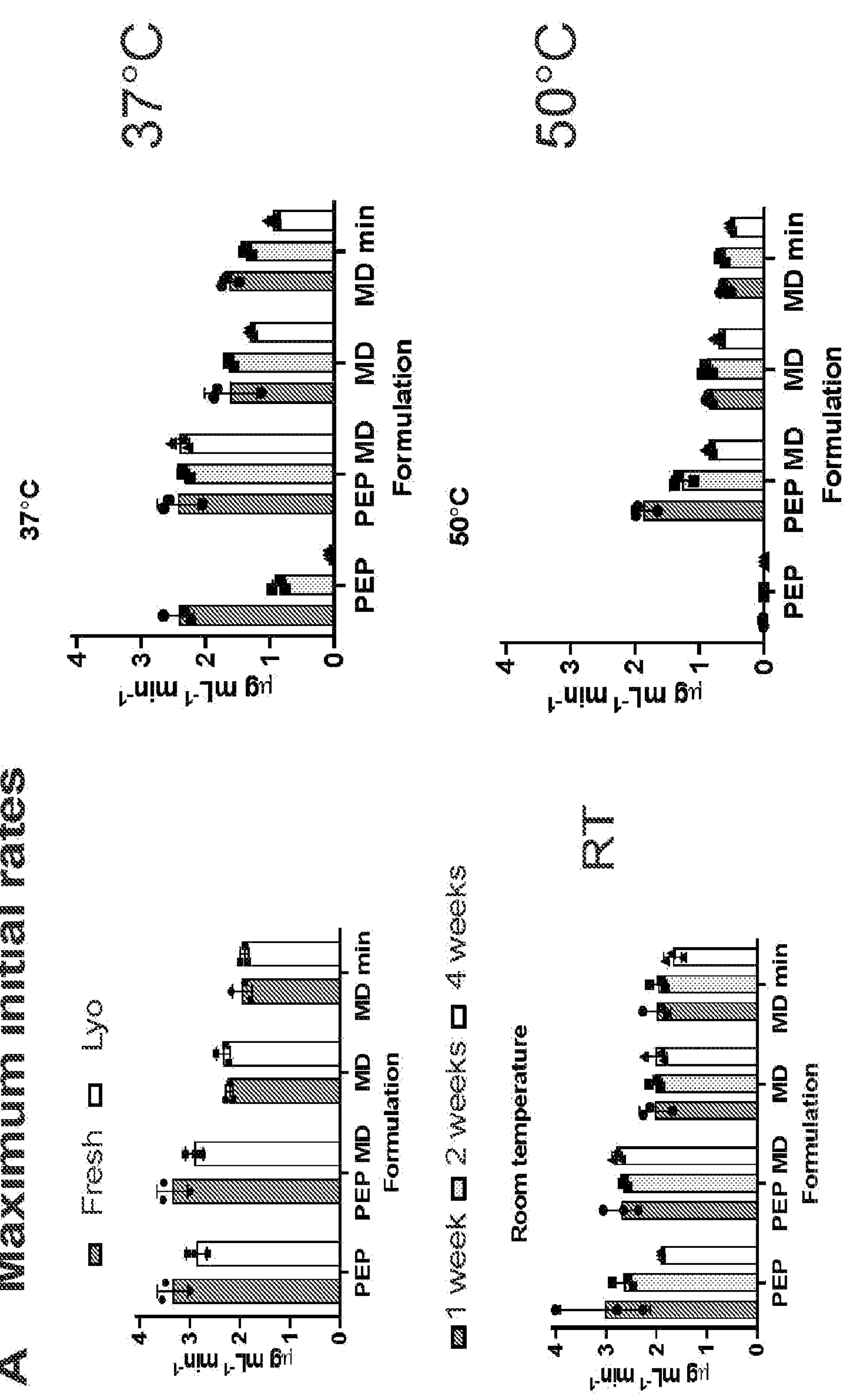
FIG. 11A-11B. Rates of sfGFP synthesis in all formulations using the iVAX extract. (A) Maximum initial rates calculated over the first 90 minutes of protein synthesis using qPCR measurement of fluorescence every 5 minutes for fresh, lyophilized, and 1, 2, and 4 weeks at room temperature, 37° C., or 50° C. storage. Fluorescence was converted from RFU to μg/mL sfGFP using standard curves with $^{14}C$-labeled sfGFP. (B) qPCR traces recording fluorescence every 5 minutes for all reaction conditions measured in RFUs over the initial 300 minutes of the reaction. While reactions were incubated in the instrument at 30° C. for 20 hours to read endpoint sfGFP, the instrument reaches the limit of detection at ~60,000 RFU, thus only initial kinetic data is shown, and maximum reached at ~60,0000 RFU is due to limit of detection of the instrument and is not representative of protein synthesis levels at that timepoint.
Figures 11A, 11B:
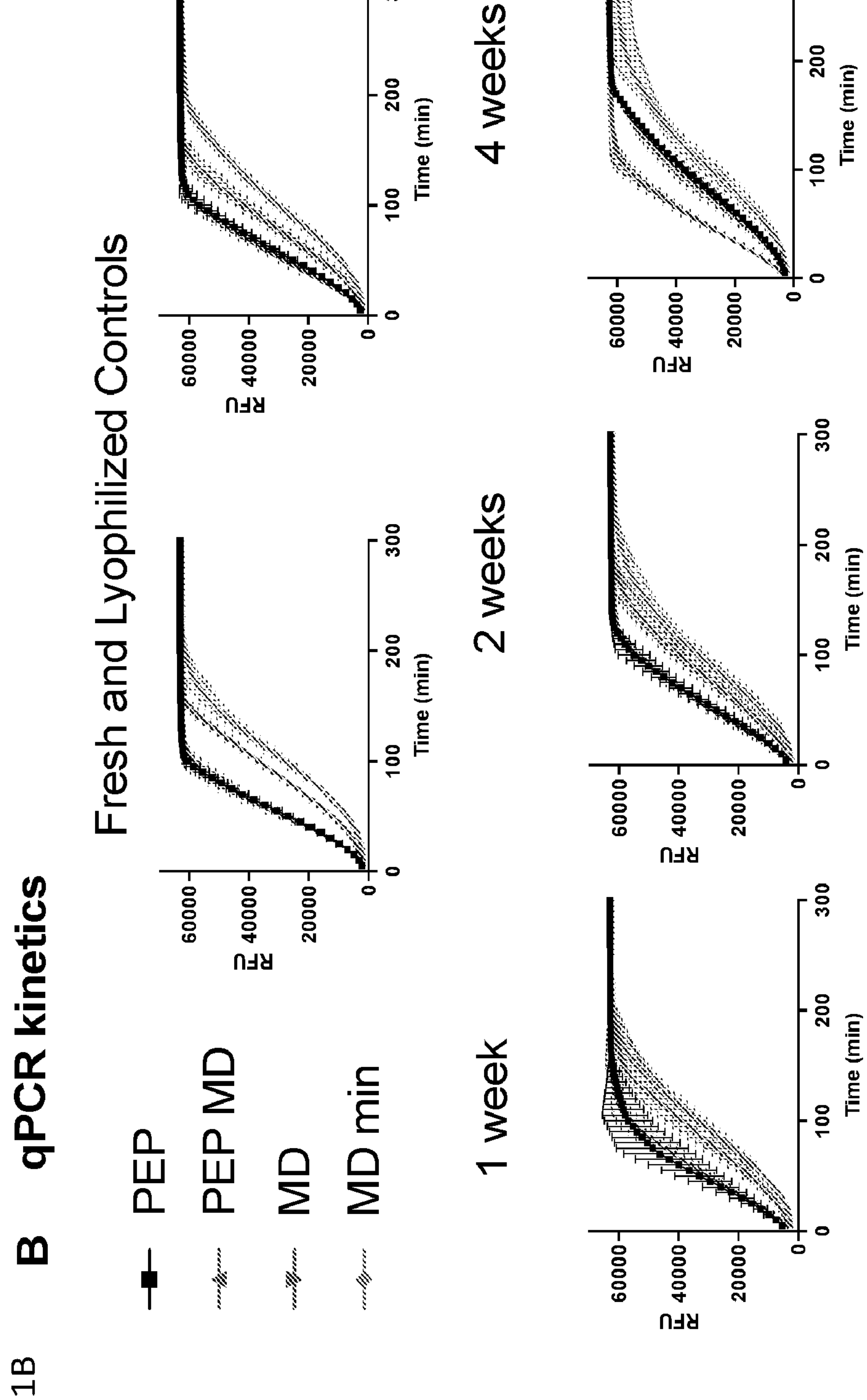
Figures 11A, 11B:
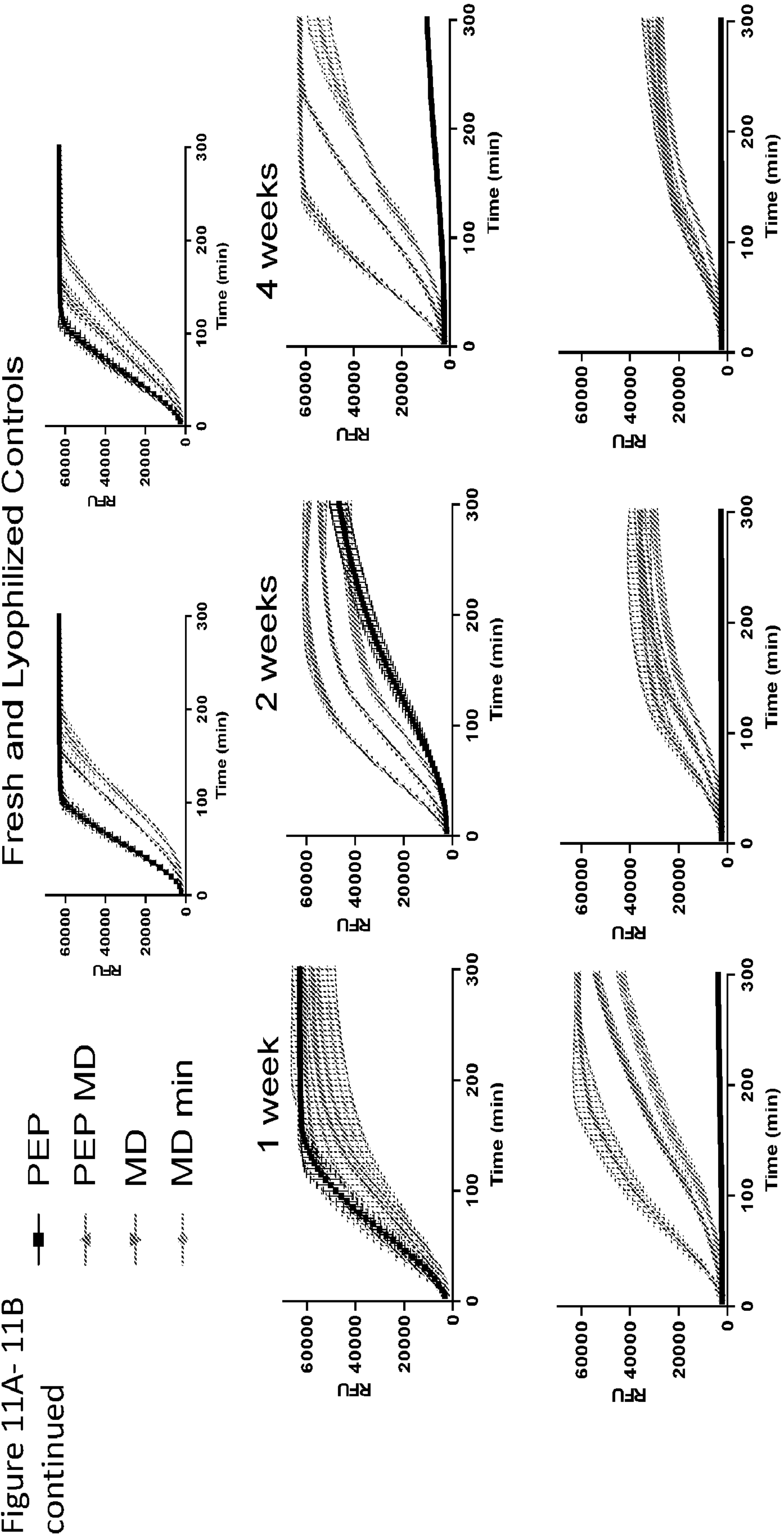
Figure 12:
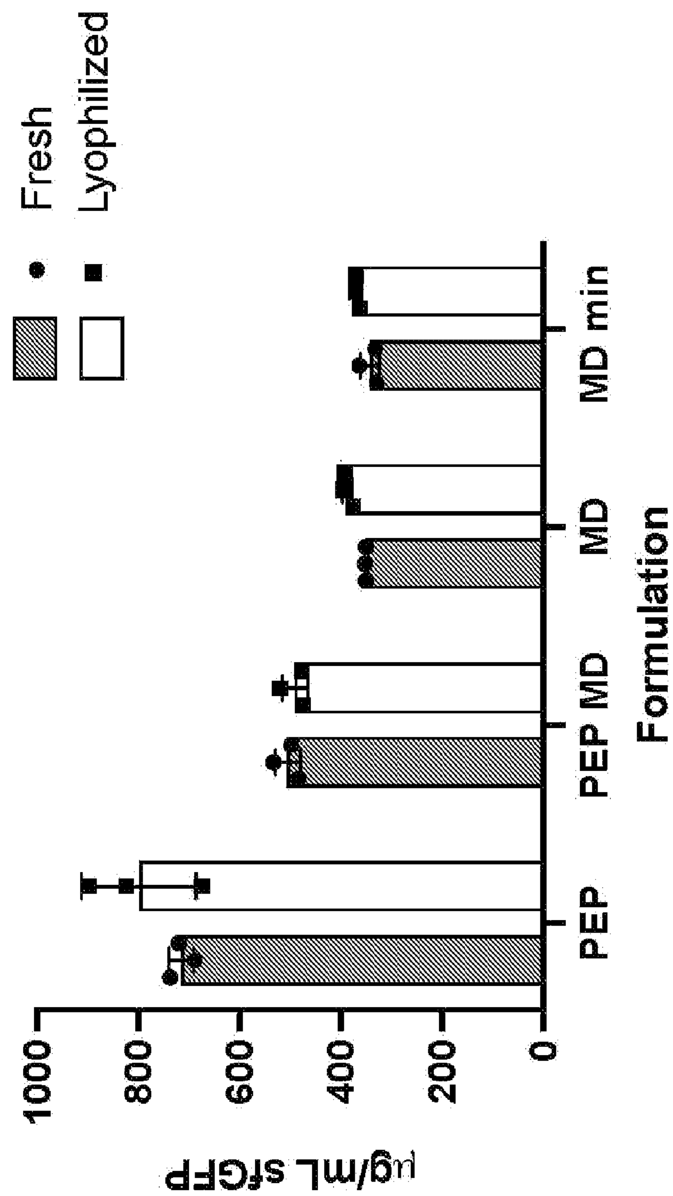
FIG. 12. sfGFP yields of fresh and lyophilized (un-stored) controls of all CFE reaction formulations with the iVAX extract. sfGFP yields of 5 μL fresh reactions that were not lyophilized (grey) and rehydrated, lyophilized reactions that were un-stored (white) after 20 hours of incubation at 30° C. using the iVAX extract. Error bars represent standard deviation of 3 CFE reaction replicates (n=3).
Figures 13A, 13B, 13C:
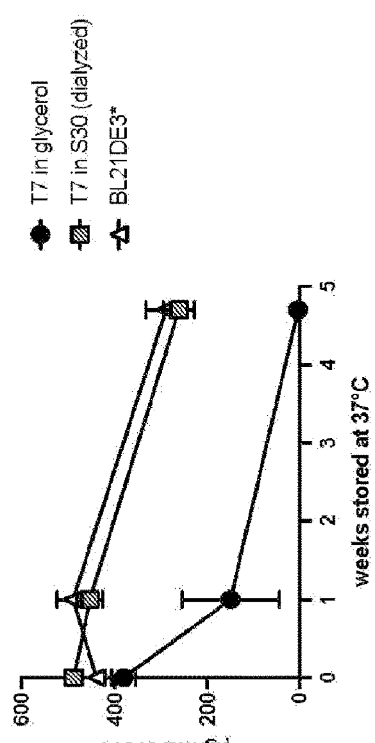
FIG. 13A-13C. Impact of glycerol (contained in purified T7) on MD formulation. (A) sfGFP yields of 5 μL fresh reactions and rehydrated, unstored, lyophilized reactions after 20 hours of incubation at 30° C. using the MD formulation in the iVAX extract. Grey bars have T7 source in 80% glycerol and white bars have the same original T7 source dialyzed into S30 buffer. (B) Reactions from the same experiment shown in A after storage at either room temperature (RT), 37° C., or 50° C. for 2 weeks. Reactions containing glycerol from the T7 stock are shown in grey while reactions with no glycerol using the dialyzed T7 stock are shown in white. (C) Endpoint sfGFP synthesis timecourse from MD formulation CFE reactions with T7 source as either T7 in glycerol (black circle), T7 in S30 buffer, dialyzed from glycerol (grey squares), or supplementing the reaction with a final concentration of 3.3% v/v BL21 Star (DE3) extract that had T7 overexpressed in the strain before lysis (white triangles). Lysate for this experiment was derived from the parental CLM24 strain not modified for glycosylation or remodeled endotoxin. Reaction conditions optimized for this strain were 8 mM $Mg^{2+}$, 50 mM phosphate, and Bis-Tris pH 10. Error bars represent standard deviation of 3 CFE reaction replicates for A, B, and C (n=3).

With an optimized, low-cost CFE formulation that could produce sufficient quantities of protein, we sought to evaluate the thermostability of this formulation after lyophilization. We lyophilized all four formulations using CLM24 ΔIpxM extracts and stored each at room temperature, 37° C., and 50° C. for 4 weeks (FIG. 3A). We rehydrated samples with 5.L of water and measured maximum initial rates over the first ninety minutes (FIGS. 3C, 3E, and 3G; FIG. 11) as well as endpoint sfGFP concentrations after 20 hours of incubation (FIGS. 3B, 3D, and 3F). Lyophilization did not reduce activity compared to fresh controls (FIG. 12), but we found that the supplementation of purified T7 RNA polymerase required for transcription (often stored in glycerol) must be dialyzed to remove glycerol (into S30 buffer) to maintain activity (FIG. 13).

After four weeks of storage at room temperature, all formulations retained activity using CLM24 ΔIpxM extracts (FIG. 3B). However, at elevated temperatures, the PEP-only formulation lost all activity after four weeks of storage at 37° C. (FIG. 3D) and after one week of storage at 50° C. (FIG. 3F), while the maltodextrin-containing formulations retained activity, albeit reduced at 50° C. (FIG. 3F). Interestingly, reactions that use maltodextrin as the energy source have slower initial rates despite similar endpoint yields, suggesting that maltodextrin is more slowly metabolized (FIGS. 3C, 3E, and 3G). While lyophilized maltodextrin-based formulations have been shown to be stable at ambient conditions,[31] this work demonstrates the first instance of high-temperature storage (50° C.) and stability of assembled CFE reactions where the energy substrate is also acting as the lyoprotectant.

Low-Cost, Thermostable CFE Enables Conjugate Vaccine Production and Storage

Figures 4A, 4B, 4C, 4D, 4E, 4F:
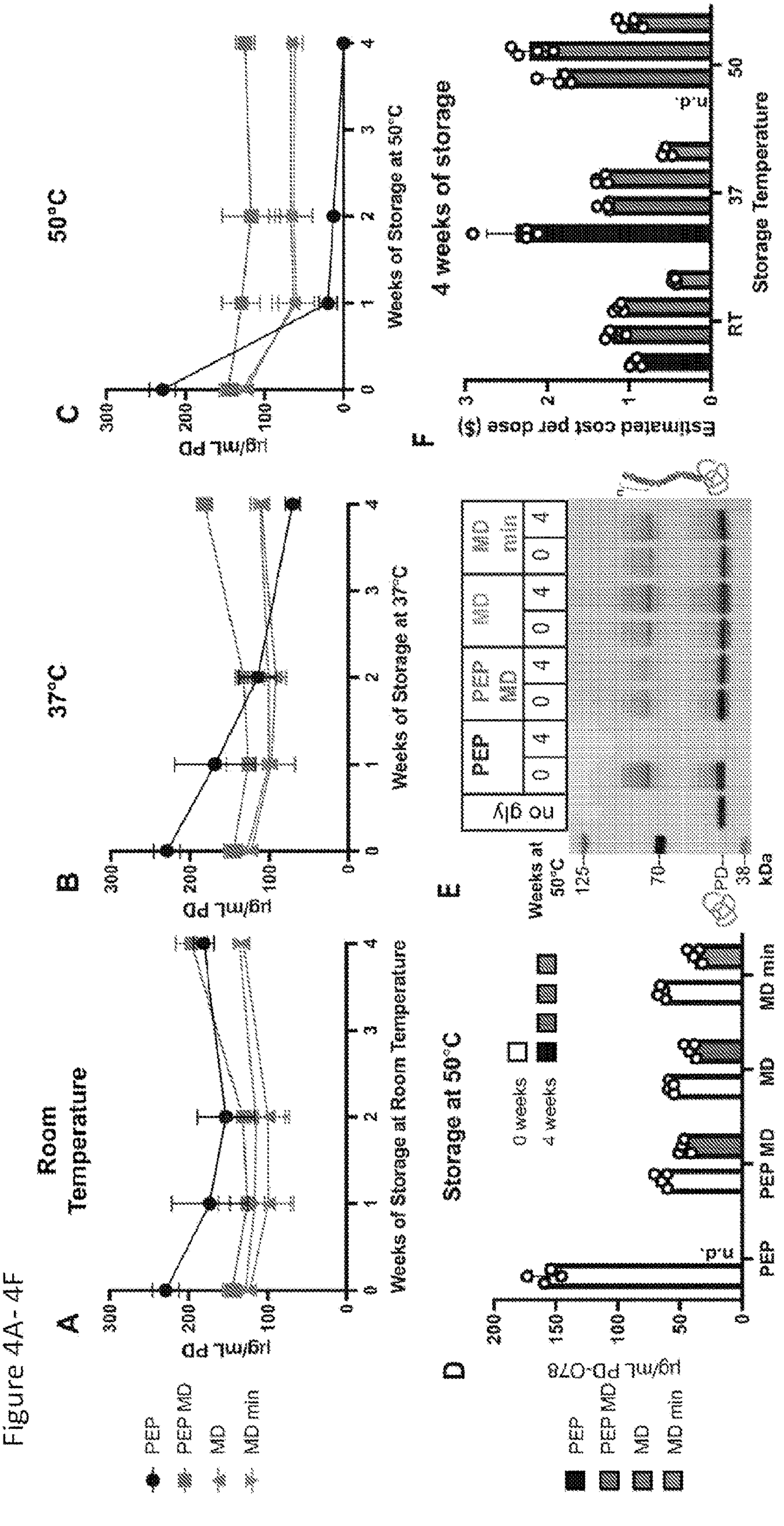
FIG. 4A-4F. Maltodextrin based formulations with iVAX extract enable production of conjugate vaccine molecules at low cost after high temperature storage. Yields of carrier protein (PD) were measured from lyophilized 15 μL reactions stored for up to 4 weeks at (A) room temperature, (B) 37° C., and (C) 50° C. CFE reactions were rehydrated with 15 μL of water and incubated at 30° C. for 20 h. Yields of glycosylated carrier protein (PD) were measured (D) and observed via Western blot (E) for reactions that were stored at 50° C. (F) Estimated cost per dose of conjugate vaccines produced by CFE reactions stored for 4 weeks at each tested temperature. Error bars represent standard deviation of 4 CFE reactions.

With a low-cost, thermostable formulation at hand, we wanted to produce and store affordable conjugate vaccine molecules. We have previously shown that coupled CFE and glycosylation (iVAX) reactions are stable at room temperature for up to three months,[5] but higher temperatures are likely encountered during distribution without cold-chain temperature control. To test elevated temperatures on storage of iVAX reactions, we considered a model conjugate vaccine for distribution in resource limited settings comprised of the O-antigen from enterotoxigenic *E. coli* ETEC O78, a strain of enterotoxigenic *E. coli* responsible for diarrheal disease, conjugated to the licensed carrier protein (PD) from *H. influenzae*.[41,42] We lyophilized iVAX reactions with CLM24 ΔIpxM extracts containing the necessary glycosylation machinery and the new CFE formulations. After storage at room temperature (FIG. 4A), 37° C. (FIG. 4B), and 50° C. (FIG. 4C) for one, two, and four weeks, we measured carrier protein (PD) produced via $^{14}$C-labeled leucine incorporation. Lyophilized reactions behaved similarly under elevated temperatures when producing sfGFP (FIG. 3) and PD (FIG. 4A-C).

Figure 14A:
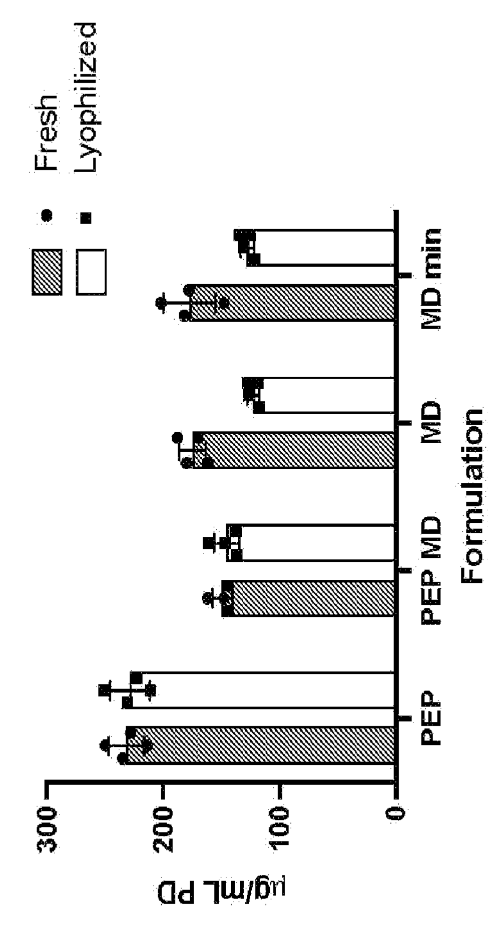
FIG. 14A-14B. PD yields and estimated cost per conjugate vaccine dose of fresh and lyophilized (un-stored) controls of all CFE reaction formulations with the iVAX extract. (A) sfGFP yields of 5 μL fresh reactions that were not lyophilized (grey) and rehydrated, lyophilized reactions that were un-stored (white) after 20 hours of incubation at 30° C. using the iVAX extract. Yields were measured using $^{14}$C-leucine incorporation. (B) Estimated cost per dose of conjugate vaccine obtained from fresh (grey) and lyophilized (white) iVAX reactions. Calculations consider estimated % glycosylation as measured by densitometry in FIG. 15D and assume a 24 g dose. Error bars represent standard deviation of 4 CFE reaction replicates (n=4).
Figure 14B:
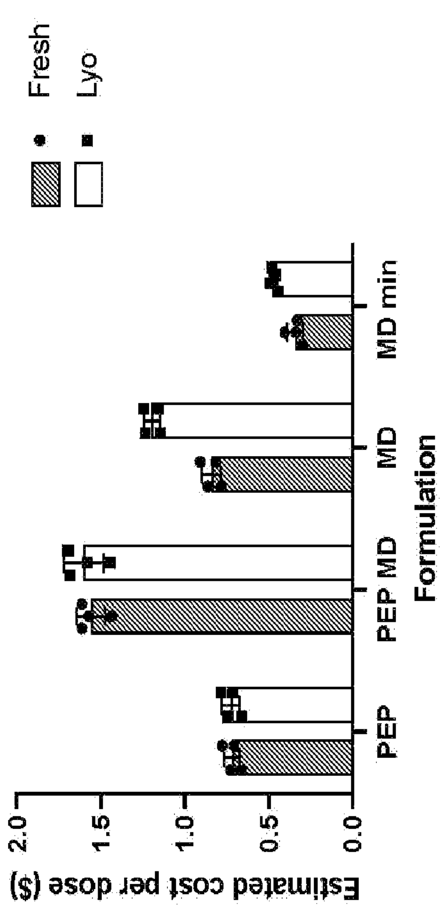
Figures 15A, 15B, 15C, 15D:
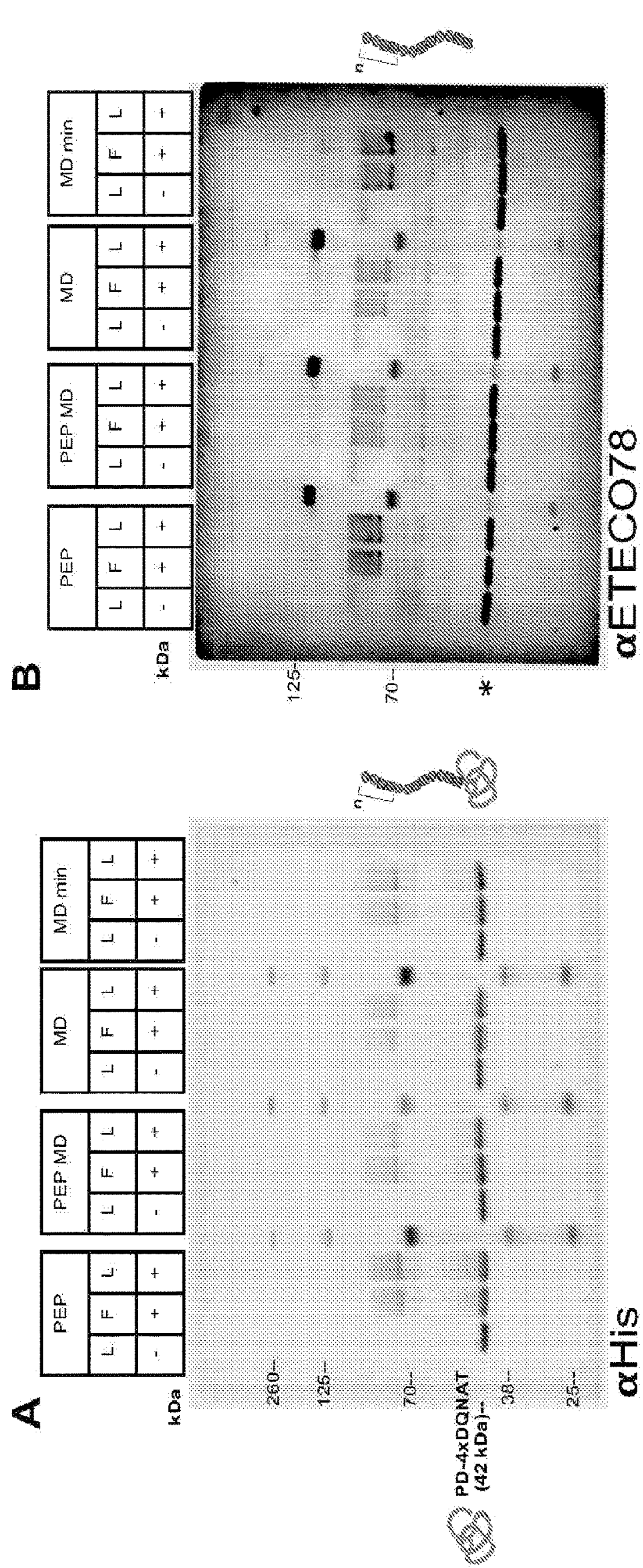
FIG. 15A-15D. Glycosylation of PD with ETEC-O78 O-antigen in iVAX reactions. (A) Anti-His Western blot against His-tagged carrier protein (PD) demonstrating glycosylation with the ETEC-O78 O-antigen in fresh and lyophilized reactions. From left to right, three control reactions are shown for each formulation (PEP, PEP MD, MD, and MD min). First a negative lyophilized control (aglycosylated PD) using an iVAX lysate with no ETEC-O78 expression is denoted as (L, −). Then, a fresh, unlyophilized control in the iVAX lysate (glycosylated PD) is denoted as (F, +). Finally, a lyophilized control in the iVAX lysate (glycosylated PD) is shown and denoted as (L, +). Equal concentration of PD as determined by $^{14}$C-leucine incorporation was loaded in each well. Each formulation is separated by a Chameleon 800 ladder annotated on the left-hand side of the blot. (B) Anti-ETEC-O78 glycan western blot demonstrating glycosylation of PD with ETEC-O78 O-antigen in fresh and lyophilized controls. Sample orientation is the same as in A. O-antigen banding is visible between the 70-kDa and 125-kDa MW markers. The band annotated with an asterisk on the left of the blot is a contaminating band found in both glycosylated and unglycosylated samples also observed in our previous work.[49]. Equal concentration of PD as determined by $^{14}$C-leucine incorporation was loaded in each well. Each formulation is separated by a Chameleon 800 ladder annotated on the left-hand side of the blot. (C) Uncropped Anti-His western blot shown in FIG. 4E demonstrating glycosylation of PD with ETEC-O78 O-antigen in samples stored for 0 weeks (lyophilized, unstored) and samples stored for 4 weeks at 50° C. The first lane has a negative glycosylation control run with an iVAX lysate with no ETEC-O78 expression in the PEP formulation that was lyophilized and then rehydrated. Then from left to right for each formulation PEP, PEP MD, MD, and MD min, there is a lyophilized sample stored for 0 weeks (lyophilized, unstored) and then a sample that was stored for 4 weeks at 50° C. Equal concentration of PD as determined by $^{14}$C-leucine incorporation was loaded in each well. For the PEP formulation after 4 weeks storage at 50° C., no protein synthesis was detected, so the volume equivalent to that used for the least concentrated sample was run on the gel as a verification. Percent glycosylation as estimated by densitometry with Image Studio Lite (Licor) software for each land is reported above the blot and used for glycoprotein calculation in main FIG. 4D. (D) Percent of glycosylated PD (glycosylated PD/total PD) was estimated for each formulation using densitometry and Image Studio Lite (Licor) software. Error bars represent standard deviation of 3 CFE reactions (n=3). Triplicate values include % glycosylation from fresh and lyophilized samples from A and lyophilized samples from C for each formulation. Values were used for cost calculation in main FIG. 4F.
Figures 15A, 15B, 15C, 15D:
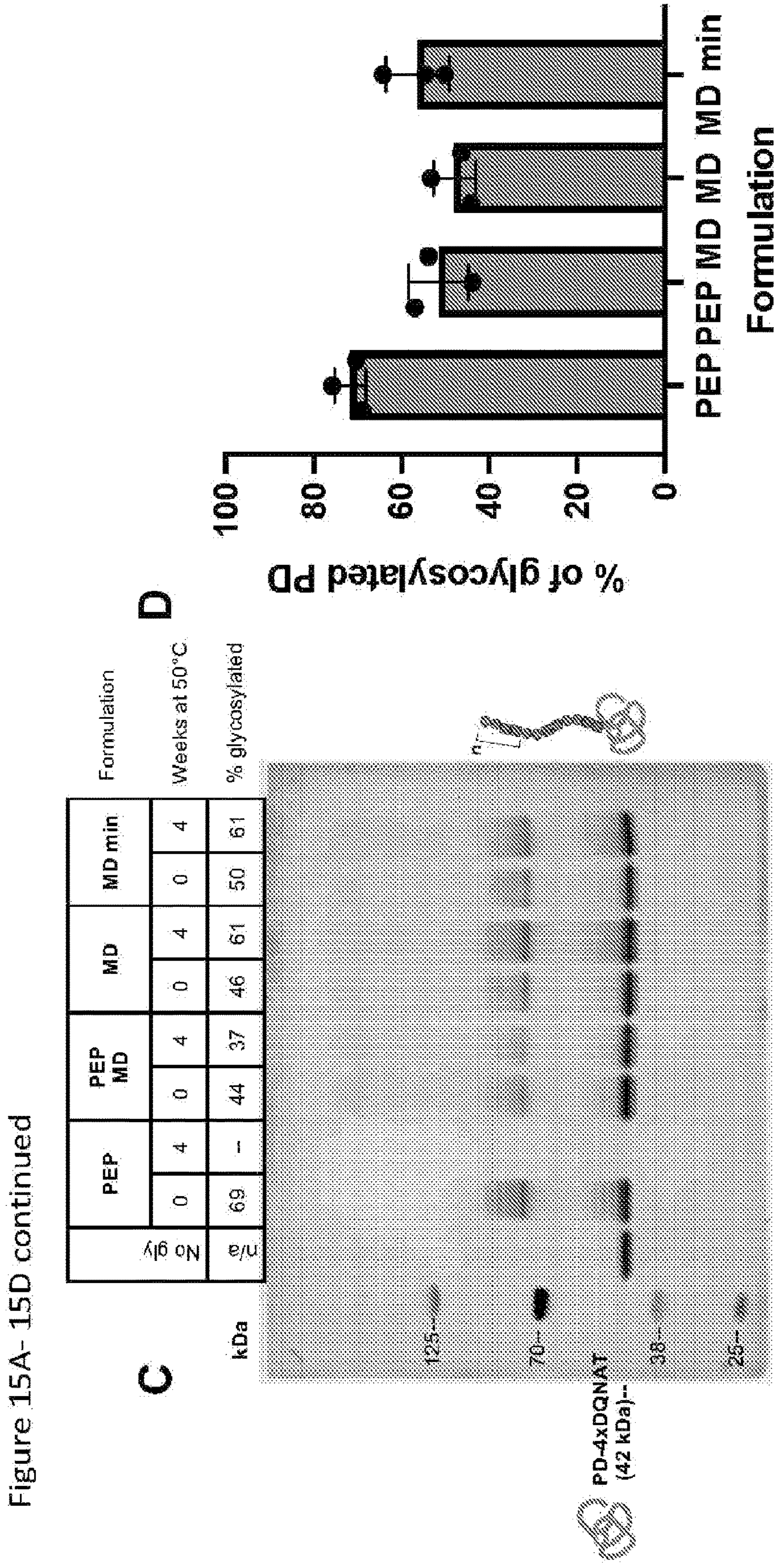

Glycosylation was initiated after 4 hours of protein synthesis (~100-200 μg/mL of carrier protein produced) (FIG. 14A) yielding at least 57 μg/mL of glycosylated PD in all conditions before storage.[20] Importantly, the glycosylation activity is retained in all formulations before storage (FIG. 15A) and preserved after four weeks of storage at 50° C. (FIG. 4E, 15C). Each formulation with protein produced can efficiently glycosylate PD as seen by the characteristic O-antigen banding pattern (varying number of repeated monomers) on the anti-His Western blot (FIG. 4E). The glycoprotein produced is also cross-reactive with serum specific for the ETEC O78 O-antigen (FIG. 15B). While maltodextrin-containing reactions slightly impair glycosylation efficiency, with ~50% glycosylation when MD is present compared to ~70% for PEP formulations (FIG. 15D), these reactions produce more protein after storage at elevated temperatures, yielding higher concentrations of glycosylated product than the PEP formulations (FIG. 4D). At 24 g of conjugate vaccine per dose, we estimated that the MD min formulation could synthesize conjugate vaccines for ~$0.50 per dose after storage at 37° C. for four weeks and ~$1.00 per dose after storage at 50° C. for four weeks (FIG. 4F), making it the most cost-effective formulation. Even before storage, the MD min formulation still has a cost benefit due to the significantly cheaper cost of raw materials in the reactions (FIG. 14B). These developments reduce the cost of iVAX reactions capable of synthesizing conjugate vaccines and enable activity after weeks of storage at elevated temperatures that are likely encountered during distribution without cold-chain temperature control.

Figures 5A, 5B, 5C:
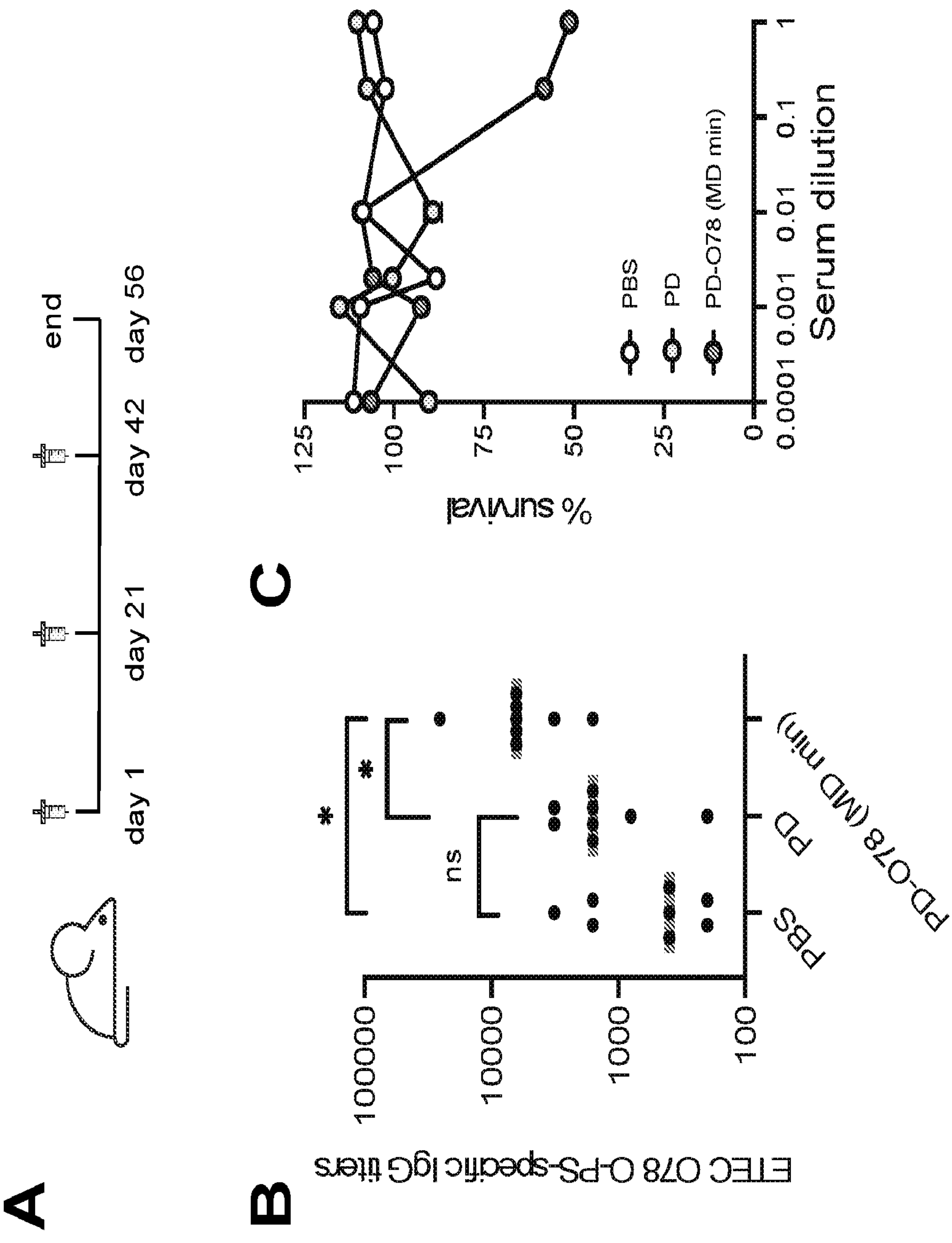
FIG. 5A-5C. Conjugate vaccines produced using the MD min CFE formulation elicit antibodies that are bactericidal. (A) Lyophilized MD min CFE reactions using iVAX extracts were used to synthesize anti-ETEC O78 conjugate vaccines for immunization studies. Groups of BALB/c mice were immunized subcutaneously with a 1:1 mixture of adjuvant and PBS or ~24 g of the following cell-free derived immunogens: unconjugated protein D (PD), or PD modified with O78 O-PS from a minimal iVAX reaction (PD-O78 (MD min)). Each group was composed of eight mice. Mice were boosted on days 21 and 42 with identical doses of antigen. (B) ETEC O78 O-PS-specific IgG titers were measured by enzyme-linked immunosorbent assay (ELISA) in endpoint (day 56) serum of individual mice (black dots) with recombinant O-PS immobilized as antigen. Mean titers of each group are also shown (red lines). Statistical significance was calculated by unpaired two-tailed t-test using GraphPad Prism 9 for MacOS software (version 9.2.0) with a single asterisk (*) indicating p-value<0.05 and ns indicating not significant. (C) Bacterial killing activity of serum antibodies corresponding to the same groups as in (A). Survival data were derived from a standard serum bactericidal assay (SBA) where dilutions of pooled sera from immunized mice were tested against ETEC O78 strain H10407 in the presence of human complement. Values for % survival were determined from the colony forming units (CFUs) counted at each individual serum dilution. Data represent means and error bars represent standard deviation.

Conjugate Vaccines Produced Using the MD Min Formulation Elicit Bactericidal Antibodies Finally, we tested the effectiveness of lyophilized PD-O78 conjugates synthesized using the MD min CFE formulation. We scaled up production, purified conjugates, and immunized 8 BALB/c mice with ~24 g of conjugate or negative control (aglycosylated PD or PBS). Mice were then boosted with 24 μg of conjugate on days 21 and 46, with serum collected on day 56 at the end of the trial (FIG. 5A). ETEC O78 O-polysaccharide (0-PS) specific antibodies were generated in mice that received purified conjugate derived from purified MD min CFE reactions that was significant over both negative controls tested (FIG. 5B). We also tested the bactericidal activity of the serum collected from mice and observed ~50% survival for one and ten-fold serum dilutions for the conjugates that was not observed with serum derived from mice who received the control treatments (FIG. 5C). Together this data shows that conjugates derived from our new cost-effective, stable, MD min formulation are effective at eliciting bactericidal antibodies against ETEC O78 O-PS. As demonstrated by the robust glycosylation profile observed in our cell-free glycosylation reactions after storage at a variety of temperatures (FIG. 4E), we expect that conjugate vaccines derived from reactions stored at elevated temperature conditions will remain effective.

DISCUSSION

Cost and stability of CFE reactions are key barriers to point-of-need use of cell-free technologies such as iVAX for glycoconjugate vaccine production. Here, we build upon previous cell-free optimizations and studies to identify a low-cost thermostable reaction formulation. A key innovation of this work is the use of maltodextrin to simultaneously stabilize lyophilized reactions at high temperature and reduce reaction cost. Maltodextrin can be used as energy in the CFE reaction and serve as a lyoprotectant without extensive optimization. To our knowledge, this is the first characterization of CFE reactions using a non-phosphorylated energy substrate at elevated temperatures (above ambient). We were further able to reduce the cost of the reaction to ~25% of the original, by identifying a maltodextrin minimal (MD min) formulation that is economically beneficial for multiple extract source strains tested and is still capable of synthesizing protein after storage for 4 weeks at 50° C. This formulation supports protein synthesis in extracts produced from the common high-yielding strain BL21 Star (DE3) as well as a specialized iVAX strain tailored to produce complex glycosylated products.

Successful conjugate vaccine distribution as determined by the MenAfriVac campaign must achieve<$0.50 per dose at extreme storage temperatures (40° C.).43,44 Importantly, we show that our low-cost CFE formulations meet these metrics and can synthesize effective model conjugate vaccine molecules against ETEC O78 after storage for up to 4 weeks at 37° C. at this price point. Additionally, the formulation is still active after storage at up to 50° C., although the price increases to $1.00 per dose. In fact, our maltodextrin minimal (MD min) system is capable of synthesizing ~40 μg/mL of glycoconjugate vaccine molecule after storage at all conditions after 4 weeks, higher than previously reported concentrations for this molecule.5 Importantly, all formulations with maltodextrin retain protein synthesis activity after high temperature storage, while activity of the original formulation (PEP) declines (37° C.) or disappears (50° C.). Our formulations achieved<$1.00 per dose for all storage temperatures tested, and the MD min formulation stored at room temperature can reach ~$0.40 per dose. These cost estimates were determined based on raw materials purchased at the laboratory scale.7 Labor and capital equipment costs required for production are highly dependent on production scale and were therefore not included. In addition, bulk purchasing of materials and supplier choice also plays a significant role in cost estimation, as demonstrated in the recent cost analysis of PEP formulations.31 We anticipate this work and the continued interest in CFE systems will lead to new metrics to more accurately predict CFE cost at a variety of scales, formal large-scale economic analyses, and further optimization of cell-free reaction formulations to improve commercial feasibility.

This work provides a valuable step in the implementation of cell-free reactions for decentralized manufacturing and builds on past work by taking advantage of the multiple properties of maltodextrin as a reaction component. Further studies on the differences between strains and their abilities to metabolize maltodextrin as an energy source are also next steps to further increase yields obtained in the system. We show that glycosylated products now join other highly sought after molecules that can be produced in lyophilized CFE systems following a range of storage conditions.19 Further optimization and scaling of this platform holds promise for next generation distributed manufacturing using an easily adapted platform for protein and glycoprotein synthesis, particularly for application in conjugate vaccine synthesis. Taken together, the generation of effective ETEC O78 conjugate vaccines in a low-cost, thermostable formulation greatly advances our iVAX platform and increases accessibility of the technology that can be used to synthesize glycoprotein vaccines in low-resource settings.

Materials and Methods

Extract Preparation

Cells were grown in shake flasks at the 1 μL scale or in a Sartorius Stedim BIOSTAT Cplus bioreactor at the 10 L scale. BL21 Star (DE3) cells were inoculated at optical density at 600 nm ($OD_{600}$)=0.08 and grown in 2×YTPG at pH 7.2 at 37° C. Cells were induced at $OD_{600}$=0.6 with 0.5 mM of IPTG to induce T7 RNA polymerase expression and harvested at $OD_{600}$=3. CLM24 ΔJpxM cells transformed with plasmids pSF-PglB-LpxE[5] and pMW07-O78[5,45,46] were inoculated at $OD_{600}$=0.08 and grown in 2×YTP with no glucose and carbenicillin at 100 g/mL and chloramphenicol at 34 g/ml supplemented at 37° C. Cells were induced at $OD_{600}$=0.8-1 with 0.02% arabinose to induce expression of PglB and the ETEC-O78 O-antigen and harvested at $OD_{600}$=3. All subsequent steps were performed on ice unless otherwise stated. Cells were harvested by centrifugation at 5,000×g for 15 minutes and then washed 3 times with S30 buffer (10 mM Tris acetate pH 8.2, 14 mM magnesium acetate, and 60 mM potassium acetate). Following washing, cells were pelleted at 7,000×g for 10 minutes, then either flash frozen and stored at ~80° C. or directly resuspended for lysis.

BL21 Star (DE3) cells were resuspended in 1 mL/g S30 buffer. Cells were then lysed using a Q125 Sonicator (Qsonica, Newtown, CT) with a 3.175 mm diameter probe at a frequency of 20 kHz and 50% amplitude. Energy was delivered to cells in pulses of 10 s followed by 1 s off until 640 J was delivered to each 1-mL aliquot of resuspended cells. Following lysis, cells were centrifuged for 12,000×g for 10 minutes. Supernatant was then collected, flash frozen and stored at −80° C. as the final extract.

CLM24 ΔIpxM cells were resuspended in 1 mL/g S30 buffer. Cells were then homogenized using an EmulsiFlex-B15 (1 μL scale) or an EmulsiFlex-C3 (10 μL scale) high-pressure homogenizer (Avestin, Inc. Ottawa, ON, Canada) with 1 pass at a pressure of ~21,000 psig. Following lysis, cells were centrifuged for 12,000×g for 10 minutes. Supernatant was then collected and incubated at 37° C. for 1 hour in a runoff reaction. Cells were then centrifuged once more at 10,000×g for 10 minutes and then the supernatant was flash frozen and stored at −80° C. as the final extract. Reagents involved in extract preparation are included in Table 2.

Plasmids

All plasmids used in this study are listed in Table 5. No new plasmids were cloned in this study, and all appropriate references are cited.

TABLE 5

Strains and plasmids used in this study.

| Strain or Plasmid | Description |
|---|---|
| BL21 Star (DE3) | *E. coli* B strain for expression. |
| CLM24 ΔIpxM[49] | *E. coli* K-12 strain CLM24 with a knockout of the aceyltransferase IpxM to alter endotoxin structure. |
| pJL1-sfGFP[50] | sfGFP variant with a C-terminal strep tag in the pJL1 expression vector, |
| pJL1-PD-4x DQNAT[49] | *H. influenzae* protein D modified with a C-terminal 4x DQNAT glycosylation sequon and a 6x His tag, recognized by *C. jejuni* PglB in the pJL1 expression vector. |
| pMW07-O78[49, 50, 51] | *E. coli* O78 O-antigen gene cluster in the pMW07 expression vector. |
| pSF-PglB-LpxE[49] | *C. jejuni* PglB with a C terminal LpxE phosphatase from *F. tularensis* and a 1x-FLAG tag in the pSF expression vector. |

CFPS Reactions

Reactions were run at the 5-μL scale in PCR tubes in a qPCR instrument set to 30° C. incubation or at the 15-μL scale in 1.5-mL microcentrifuge tubes in a 30° C. incubator (Axygen). Reactions were run for 20 hours when synthesizing sfGFP. Reactions containing lyoprotectants were supplemented with trehalose (Sigma, T0167), sucrose (Sigma, S0389), Dextran 70 (TCI chemicals, D1449), glucose (Sigma, G8270), maltose (Sigma, M9171), or maltodextrin-dextrose equivalent 4.0-7.0 (Sigma, 419672), at the appropriate final concentrations (10-100 mg/mL) as described in the text. A fresh stock solution of 300 mg/mL maltodextrin was prepared fresh before reaction set up and added to CFPS reactions at the appropriate concentration. All other lyoprotectants were prepared and stored at −20° C.

Reactions for each formulation were prepared as described below and in Table 4.

PEP: Each reaction was prepared as described previously[20] unless otherwise noted, to contain 13.33 ng/uL plasmid, 30% (vol./vol. %) S12 extract, and the following: 10 mM magnesium glutamate (Sigma, 49605), 10 mM ammonium glutamate (Biosynth, FG28929), 130 mM potassium glutamate (Sigma, G1501), 1.2 mM adenosine triphosphate (Sigma A2383), 0.85 mM guanosine triphosphate (Sigma, G8877), 0.85 mM uridine triphosphate (Sigma U6625), 0.85 mM cytidine triphosphate (Sigma, C1506), 0.034 mg/mL folinic acid, 0.171 mg/mL *E. coli* tRNA (Roche 10108294001), 2 mM each of 20 amino acids, 30 mM phosphoenolpyruvate (PEP, Roche 10108294001), 0.4 mM nicotinamide adenine dinucleotide (Sigma N8535-15VL), 0.27 mM coenzyme-A (Sigma C3144), 4 mM oxalic acid (Sigma, P0963), 1 mM putrescine (Sigma, P5780), 1.5 mM spermidine (Sigma, S2626), and 57 mM HEPES (Sigma, H3375). T7 was supplemented to reactions at a final concentration of 15-20 g/mL using the iVAX strain either in 50% glycerol or dialyzed into S30 buffer supplemented with 2 mM DTT.

PEP MD: Maltodextrin at a final concentration of 60 mg/mL was supplemented to the PEP reaction formulation described above. See Table 4 for more details.

MD: Maltodextrin at a final concentration of 60 mg/mL was supplemented to the PEP reaction formulation described above and PEP was removed. Potassium phosphate dibasic was supplemented to the PEP reaction formulation at a final concentration of 75 mM unless otherwise noted. Potassium phosphate dibasic (Sigma, 60353) was prepared and pH was adjusted to 7.2 with acetic acid. For BL21 Star (DE3) extract-based reactions, Bis-Tris (Sigma, B9754) with unadjusted pH was added at a concentration of 57 mM and HEPES was removed. See Table 4 for more details.

MD min: Reactions were prepared according to the MD reaction formulation described above with the removal of tRNA and CoA. NTPs were also replaced by equal concentration of NMPs (CMP: Sigma C1006, UMP: Sigma U6375, AMP: Sigma 01930, GMP: Sigma G8377). NMPs were prepared at a stock concentration of 0.5 M by dissolving in nuclease free water and pH was adjusted to 7.2 with acetic acid. See Table 4 for more details.

Lyophilization and Packaging

CFPS reactions were set up as described above in the CFPS Reactions methods section. Reactions were set up on ice and aliquoted into PCR strip tubes with 1 hole in the lid created by an 18-gauge needle. Samples were kept on ice in aluminum blocks (Cole-Parmer 6361504) and then samples (in blocks) were flash frozen in liquid nitrogen. Frozen samples in blocks were then transferred to a multi-tainer manifold adapter on a VirTis Benchtop Pro Lyophilizer (SP scientific). Lyophilization was performed at 100 mT and a condenser set to −80° C. Samples were lyophilized overnight for 16-20 hours. Following lyophilization, samples were packaged (all replicates stored together for each tested time and temperature condition) in a FoodSaver bag with 2-4 Dri-Card desiccant cards and then vacuum sealed under ambient conditions with a FoodSaver vacuum sealer. Packaged samples were then stored at room temperature at the bench (−22° C.), or in incubators set to either 37° C., or 50° C. as indicated for the appropriate storage time. Lyophilized controls were rehydrated immediately after removal from the lyophilizer and not stored or packaged in a vacuum sealed bag.

Protein Quantification

For sfGFP measurement, 2 μL of CFPS reaction was diluted with 48 μL of nanopure water in a black costar 96 well plate. Fluorescence was read on a plate reader and converted to μg/mL sfGFP using a standard curve made from sfGFP measured by $C^{14}$ incorporation.

For initial sfGFP synthesis rate measurements, fluorescence was measured every 5 minutes by the qPCR machine. Initial rates were calculated by taking the maximum slope over the first 90 minutes of the cell-free protein synthesis reaction. Relative fluorescence units measured by the qPCR were converted to μg/mL of sfGFP using a standard curve. To calculate the maximum initial slope over the first 90 minutes, a sliding window of 5 time points was used. For each window, the slope was determined based on a regression line fitting the five time points. This was repeated over the 90 minutes, advancing the starting time point of the window by 1 each time. The maximum initial slope was determined independently for each of the 3 replicates, which were then averaged together to determine the overall average maximum initial slope. This process was completed for each individual reaction condition.

For PD synthesis, 15-μL reactions containing all reagents except the DNA template were lyophilized and then rehydrated with 15 μL of nuclease free water containing 200 ng of PD-4×DQNAT (or no DNA in control reactions), and 10 μM of $C^{14}$ Leucine (PerkinElmer). Following centrifugation at 16,000×g for 15 minutes, 5 μL of the soluble fraction of each reaction was treated with 5 μL of 0.5 M KOH for 20 minutes at 37° C. Following incubation, 4 μL of the sample was added to two filtermats (PerkinLermer Printer Filtermat A 1450-421). After the filtermat dried, one filtermat was washed 3 times for 15 minutes with 5% w/v TCA at 4° C. and once with Ethanol for 10 minutes at room temperatures. After the washed filtermat dried, scintillation wax (PerkinElmer MeltiLex A 1450-441) was melted on both mats and counts were measured using a Microbeta2 scintillation counter (PerkinElmer). Background radioactivity was measured in CFGpS reactions with no template DNA and subtracted before calculating protein yields. Fraction of incorporated leucine (washed/unwashed counts) was multiped by the overall leucine concentration in the reaction and the molecular weight of pJL1-PD-4×DQNAT (Table 5). The amount of protein produced was determined by dividing this value by the number of leucines present in the protein.

Cell-Free Glycoprotein Synthesis Reaction

For PD synthesis and glycosylation, 15 μL reactions were rehydrated with nuclease free water (Ambion) supplemented with 200 ng of pJl1-PD-4×DQNAT and 10 μM of $C^{14}$ Leucine for a total volume of 15 μL added to the reactions. After rehydration, reactions were incubated for 4 hours at 30° C. After 4 hours, 0.1% (wt/vol) DDM and 25 mM $MnCl_2$ were added to each reaction to initiate glycosylation and incubated at 30° C. for an additional 16 hours. Before analysis, samples were centrifuged at 16,000×g for 15 minutes and the soluble fraction was removed. The soluble fraction of each reaction was used to measure yields of the accepter protein PD-4×DQNAT by radioactive counting and to load on western blot to verify glycosylation.

Western Blotting

Samples were loaded on 4-12% Bis-Tris gels and run with SDS-MOPS running buffer supplemented with NuPAGE antioxidant. Samples were then transferred to Immobilon-β-polyvinylidene difluoride (PVDF) 0.45 m membranes (Millipore, USA) for 55 minutes at 80 mA per blot using a semi-dry transfer cell. Membranes were blocked for 1 hour at room temp or overnight at 4° C. in Intercept Blocking Buffer (Licor). Primary antibodies used were anti-His (Abcam, ab1187) at 1:7,500 dilution or anti-ETEC-O78 antigen (Abcam, ab78826) at 1:2,500 dilution in Intercept blocking buffer with 0.2% Tween20 were incubated for 1 hour at room temp or overnight at 4° C. A fluorescent goat, anti-rabbit antibody GAR-680RD (Licor) was used as the secondary antibody at 1:10,000 dilution in Intercept blocking buffer, 0.2% Tween20 and 0.1% SDS for both anti-His and anti-O78 glycan blots. Blots were washed 6 times for 5 minutes after each of the blocking, primary, and secondary antibody incubations using 1×PBST. Blots were imaged with Licor Image studio and analyzed by densitometry using Licor Image studio Lite. Fluorescence background was subtracted from each membrane before densitometry was performed.

Cost Analysis

The cost of each CFPS reaction formulation was estimated using lab scale quantities of reagents from vendors utilized in this study (Table 3). Labor and equipment costs are not considered in these estimations. For extract cost estimations, it is assumed that 4 mL of extract are produced per L of cell culture and 30% v/v extract is added to CFE reactions. A "base" extract cost of only the components added to the culture for all strains is considered, to make cost estimates more generalizable. The cost of variable components such as inducers and antibiotics are approximately the same for both strains used in this study and are dependent on strain and plasmid used to make extract (Table 2). Glycosylation cofactors are included in the vaccine cost estimates. Vaccine cost estimates assume a 24-ag conjugate vaccine dose and take into account the glycosylation efficiency (amount of PD successfully glycosylated) determined in FIG. 15D. Table 1-4 includes references, assumptions and detailed cost calculations for each reaction component.

Mouse Immunizations

Glycoconjugate production: Cell-free glycoprotein synthesis reactions were run as described above using the MD min CFE reaction formulation and were scaled up to 5 mL in 50 mL falcon tubes. Reactions were lyophilized overnight for 16-20 hours and then rehydrated with 5 mL of nuclease free water and incubated at 30° C. for 1 hour. Following 1 hour of protein synthesis, glycosylation was initiated and reactions were incubated at 30° C. overnight. The unglycosylated PD negative control was synthesized using the PEP CFE formulation in S30 iVAX extract without the ETEC-O78 pathway overexpressed.[5]

Glycoconjugate Purification: CFGpS reactions were centrifuged at 20,000×g for 10 minutes. The supernatant was then mixed with 0.5 mL of Ni-NTA Agarose resin (Qiagen), equilibrated with 50 mM $NaH_2PO_4$, 300 mM NaCl, 10 mM imidazole, per 1 mL of CFE reaction and incubated with agitation for 2-4 hours at 4° C. Purification of His-tagged carrier protein (glycosylated and aglycosylated) was carried out according to manufacturer's protocol as follows. Following incubation with resin, CFE reaction and resin slurry was loaded onto polypropylene columns (Bio-Rad) and washed 2 times with 6 column volumes of buffer containing 50 mM $NaH_2PO_4$, 300 mM NaCl, and 20 mM imidazole. Protein was eluted with 50 mM $NaH_2PO_4$, 300 mM NaCl, and 300 mM imidazole. The most concentrated elution fractions were pooled and concentrated to −2 mg/mL, then dialyzed into sterile endotoxin free PBS and stored at 4° C. Purification fractions were analyzed on an SDS-PAGE gel and Coomassie stained. Densitometry (Licor ImageStudio) of carrier protein/total protein from SDS-PAGE was used to account for percent purity and multiplied by total A280 protein concentration as measured by nanodrop to determine conjugate concentration for mouse immunizations.

Mouse immunizations: Groups of eight 6-week-old female BALB/c mice (Harlan Sprague Dawley) were immunized with 50 μL of sterile PBS (pH 7.4, Fisher Scientific) or formulations containing unconjugated nonacylated protein D (PD) from *Haemophilus influenzae* made using the PEP CFE formulation in S30 iVAX extract without the ETEC-O78 pathway overexpressed, or PD modified with ETEC O78 O-PS made using the MD min CFE formulation (PD-O78 (MD min)). The amount of antigen in each preparation was normalized to ensure that ~24 g of unmodified protein or conjugate was administered per injection. Purified protein groups formulated in PBS were mixed with an equal volume of Adju-Phos aluminium phosphate adjuvant (InvivoGen) before injection. Each group of mice was immunized subcutaneously with vaccine candidates or controls, then boosted 21 and 42 days after the initial immunization. For antibody titering, blood was obtained on days 0, 35, and 49 via submandibular collection, and at study termination on day 56 via cardiac puncture. For bacterial killing assays, final blood collections for all the mice within each group were pooled. All procedures were carried out in accordance with protocol 2012-0132 approved by the Cornell University Institutional Animal Care and Use Committee.

Enzyme-Linked Immunosorbent Assay (ELISA)

The plasmid pMW07-O78 encoding the pathway for E. co/i ETEC O78 O-antigen biosynthesis was used to transform *E. coli* JC8031 competent cells. The resulting cells were used to prepare O78 LPS antigen in house by hot phenol water extraction after DNase I (Sigma) and proteinase K (Invitrogen) treatment, as described elsewhere.[47] Extracted LPS was purified using a PD-10 desalting column packed with Sephadex G-25 resin (Cytiva), and concentration was determined using a purpald assay.[48] 96-well plates (MaxiSorp; Nunc Nalgene) were incubated with 0.5 g/mL of purified O78 LPS diluted in PBS, pH 7.4, 25 L/well, at 4° C. overnight. Plates were blocked in blocking buffer overnight at 4° C. with 5% (w/v) nonfat dry milk (Carnation) in PBS, then washed three times with 200 μL PBS-T (PBS, 0.05% Tween 20) per well. Serum samples isolated from the collected blood draws of immunized mice were appropriately serially diluted in triplicate in blocking buffer and added to the plates for 2 hours at 37° C. Plates were washed three times with PBS-T (+0.03% BSA (w/v)), then incubated for 1 hour at 37° C. in the presence of a horseradish peroxidase-conjugated antibody, goat anti-mouse IgG (Abcam, 1:25,000 dilution). After three PBS-T+0.3% BSA washes, 50 μL of 3,3'-5,5'-tetramethylbenzidine substrate (1-Step Ultra TMB-ELISA; Thermo Fisher Scientific) was added to each well, and the plates were incubated at room temperature in the dark for 30 min. The reaction was stopped by adding 50 μL of 2 M $H_2SO_4$, and absorbance was measured at a wavelength of 450 nm using a FilterMax F5 microplate spectrophotometer (Agilent). Serum antibody titers were determined by measuring the lowest dilution that resulted in signals that were 3 standard deviations above the background controls of no serum. Statistical significance was determined in GraphPad Prism 9 for MacOS (Version 9.2.0) using an unpaired two-tailed t-test.

Serum Bactericidal Assay (SBA)

A modified version of a previously described SBA method was followed.[45] ETEC H10407 cells were grown overnight from a frozen glycerol stock, then seeded 1:20 in Luria Bertani (LB) medium. Log-phase grown bacteria were harvested, adjusted to an $OD_{600}$ of 0.1, then further diluted 1:5,000 in Hanks' Balanced Salt Solution with 0.5% bovine serum albumin (BSA) (Sigma Aldrich). Assay mixtures were prepared in 96-well microtiter plates by combining 20 μL of serially diluted heat-inactivated test serum (with dilutions ranging from 1-104), and 10 μL of diluted bacterial suspension. After incubation with shaking for 60 minutes at 37° C., 10 μL of active or inactive complement source was added to each well, to a final volume percent of 25%. Heat-inactivated complement was prepared by thawing an aliquot of active pooled human complement serum (Innovative Research, ICSER1IML), incubating in a 56° C. water bath for 30 minutes, and cooling at room temperature. Assay plates were incubated with shaking at 37° C. for 60-90 minutes, then 10 μL was plated from each well (diluted to 50 μL in LB) on LB agar plates. Serum samples were tested and plated in duplicate, and colonies were counted (Promega Colony Counter) after 16-18 hours of incubation at 30° C. Colony forming units (CFUs) were counted for each individual serum dilution, and SBA titers were determined by calculating percent survival at various serum dilutions. Data was plotted as percentage survival versus serum dilution.

REFERENCES

1. Karim, A. S. et al. In vitro prototyping and rapid optimization of biosynthetic enzymes for cell design. Nat. Chem. Biol. 16, 912-919 (2020).
2. Rasor, B. J., Yi, X., Brown, H., Alper, H. S. & Jewett, M. C. An integrated in vivo/in vitro framework to enhance cell-free biosynthesis with metabolically rewired yeast extracts. Nat. Commun. 12, 5139 (2021).
3. Chen, Z. et al. De novo design of protein logic gates. Science 368, 78-84 (2020).

4. Zubi, Y. S. et al. Metal-Responsive Regulation of Enzyme Catalysis using Genetically Encoded Chemical Switches. ChemRxiv (2021) doi:10.33774/chemrxiv-2021-9q174.
5. Stark, J. C. et al. On-demand biomanufacturing of protective conjugate vaccines. Sci Adv 7, (2021).
6. Kim, D.-M. & Swartz, J. R. Efficient production of a bioactive, multiple disulfide-bonded protein using modified extracts of *Escherichia coli*. Biotechnol. Bioeng. 85, 122-129 (2004).
7. Silverman, A. D., Karim, A. S. & Jewett, M. C. Cell-free gene expression: an expanded repertoire of applications. Nat. Rev. Genet. 21, 151-170 (2020).
8. Hunt, A. C., Vögeli, B., Kightlinger, W. K. & Yoesep, D. J. A high-throughput, automated, cell-free expression and screening platform for antibody discovery. bioRxiv (2021).
9. Zawada, J. F. et al. Microscale to manufacturing scale-up of cell-free cytokine production—a new approach for shortening protein production development timelines. Biotechnol. Bioeng. 108, 1570-1578 (2011).
10. Hunt, J. P., Yang, S. O., Wilding, K. M. & Bundy, B. C. The growing impact of lyophilized cell-free protein expression systems. Bioengineered 8, 325-330 (2017).
11. McNerney, M. P. et al. Point-of-care biomarker quantification enabled by sample-specific calibration. Sci Adv 5, eaax4473 (2019).
12. Liu, X. et al. Design of a Transcriptional Biosensor for the Portable, On-Demand Detection of Cyanuric Acid. ACS Synth. Biol. 9, 84-94 (2020).
13. Thavarajah, W. et al. Point-of-Use Detection of Environmental Fluoride via a Cell-Free Riboswitch-Based Biosensor. ACS Synth. Biol. 9, 10-18 (2020).
14. Pardee, K. et al. Rapid, Low-Cost Detection of Zika Virus Using Programmable Biomolecular Components. Cell 165, 1255-1266 (2016).
15. Pardee, K. et al. Portable, On-Demand Biomolecular Manufacturing. Cell 167, 248-259.e12 (2016).
16. Salehi, A. S. M. et al. Cell-free protein synthesis of a cytotoxic cancer therapeutic: Onconase production and a just-add-water cell-free system. Biotechnol. J. 11, 274-281 (2016).
17. Karig, D. K., Bessling, S., Thielen, P., Zhang, S. & Wolfe, J. Preservation of protein expression systems at elevated temperatures for portable therapeutic production. J. R. Soc. Interface 14, (2017).
18. Yang, J., Cui, Y., Cao, Z., Ma, S. & Lu, Y. Strategy exploration for developing robust lyophilized cell-free systems. Biotechnology Notes 2, 44-50 (2021).
19. Wilding, K. M., Zhao, E. L., Earl, C. C. & Bundy, B. C. Thermostable lyoprotectant-enhanced cell-free protein synthesis for on-demand endotoxin-free therapeutic production. N. Biotechnol. 53, 73-80 (2019).
20. Hershewe, J. M. et al. Improving cell-free glycoprotein synthesis by characterizing and enriching native membrane vesicles. Nat. Commun. 12, 2363 (2021).
21. Rappuoli, R., De Gregorio, E. & Costantino, P. On the mechanisms of conjugate vaccines. Proceedings of the National Academy of Sciences of the United States of America vol. 116 14-16 (2019).
22. Jin, C. et al. Efficacy and immunogenicity of a Vi-tetanus toxoid conjugate vaccine in the prevention of typhoid fever using a controlled human infection model of *Salmonella Typhi*: a randomised controlled, phase 2b trial. Lancet 390, 2472-2480 (2017).
23. Trotter, C. L. et al. Optimising the use of conjugate vaccines to prevent disease caused by *Haemophilus influenzae* type b, *Neisseria meningitidis* and *Streptococcus pneumoniae*. Vaccine 26, 4434-4445 (2008).
24. Micoli, F., Costantino, P. & Adamo, R. Potential targets for next generation antimicrobial glycoconjugate vaccines. FEMS Microbiol. Rev. 42, 388-423 (2018).
25. Calhoun, K. A. & Swartz, J. R. An economical method for cell-free protein synthesis using glucose and nucleoside monophosphates. Biotechnol. Prog. 21, 1146-1153 (2005).
26. Calhoun, K. A. & Swartz, J. R. Energizing cell-free protein synthesis with glucose metabolism. Biotechnol. Bioeng. 90, 606-613 (2005).
27. Anderson, M. J., Stark, J. C., Hodgman, C. E. & Jewett, M. C. Energizing eukaryotic cell-free protein synthesis with glucose metabolism. FEBS Lett. 589, 1723-1727 (2015).
28. Caschera, F. & Noireaux, V. Synthesis of 2.3 mg/ml of protein with an all *Escherichia coli* cell-free transcription-translation system. Biochimie 99, 162-168 (2014).
29. Caschera, F. & Noireaux, V. A cost-effective polyphosphate-based metabolism fuels an all *E. coli* cell-free expression system. Metab. Eng. 27, 29-37 (2015).
30. Wang, Y. & Zhang, Y.-H. P. Cell-free protein synthesis energized by slowly-metabolized maltodextrin. BMC Biotechnol. 9, 58 (2009).
31. Guzman-Chavez, F. et al. Constructing Cell-Free Expression Systems for Low-Cost Access. ACS Synth. Biol. (2022) doi:10.1021/acssynbio.1c00342.
32. Kim, H.-C., Kim, T.-W. & Kim, D.-M. Prolonged production of proteins in a cell-free protein synthesis system using polymeric carbohydrates as an energy source. Process Biochem. 46, 1366-1369 (2011).
33. Cai, Q. et al. A simplified and robust protocol for immunoglobulin expression in *Escherichia coli* cell-free protein synthesis systems. Biotechnol. Prog. 31, 823-831 (2015).
34. Kim, T.-W. et al. An economical and highly productive cell-free protein synthesis system utilizing fructose-1,6-bisphosphate as an energy source. Journal of Biotechnology vol. 130 389-393 (2007).
35. Gregorio, N. E. et al. Unlocking Applications of Cell-Free Biotechnology through Enhanced Shelf Life and Productivity of *E. coli* Extracts. ACS Synth. Biol. 9, 766-778 (2020).
36. Tonnis, W. F. et al. Size and molecular flexibility of sugars determine the storage stability of freeze-dried proteins. Mol. Pharm. 12, 684-694 (2015).
37. Jung, J. K. et al. Cell-free biosensors for rapid detection of water contaminants. Nat. Biotechnol. 38, 1451-1459 (2020).
38. Chang, L. L. & Pikal, M. J. Mechanisms of protein stabilization in the solid state. J. Pharm. Sci. 98, 2886-2908 (2009).
39. Hammerling, M. J., Warfel, K. F. & Jewett, M. C. Lyophilization of premixed COVID-19 diagnostic RT-qPCR reactions enables stable long-term storage at elevated temperature. Biotechnology Journal vol. 16 2000572 (2021).
40. Smith, M. T., Berkheimer, S. D., Werner, C. J. & Bundy, B. C. Lyophilized *Escherichia coli*-based cell-free systems for robust, high-density, long-term storage. Biotechniques 56, 186-193 (2014).
41. Khalil, I. et al. Enterotoxigenic *Escherichia coli* (ETEC) vaccines: Priority activities to enable product development, licensure, and global access. Vaccine 39, 4266-4277 (2021).

42. von Mentzer, A. et al. Identification of enterotoxigenic *Escherichia coli* (ETEC) clades with long-term global distribution. Nat. Genet. 46, 1321-1326 (2014).

43. Tiffay, K., Jodar, L., Kieny, M.-P., Socquet, M. & LaForce, F. M. The Evolution of the Meningitis Vaccine Project. Clin. Infect. Dis. 61 Suppl 5, S396-403 (2015).

44. Zipursky, S. et al. Benefits of using vaccines out of the cold chain: delivering meningitis A vaccine in a controlled temperature chain during the mass immunization campaign in Benin. Vaccine 32, 1431-1435 (2014).

45. Valentine, J. L. et al. Immunization with Outer Membrane Vesicles Displaying Designer Glycotopes Yields Class-Switched, Glycan-Specific Antibodies. Cell Chem Biol 23, 655-665 (2016).

46. Çelik, E. et al. Glycoarrays with engineered phages displaying structurally diverse oligosaccharides enable high-throughput detection of glycan-protein interactions. Biotechnol. J. 10, 199-209 (2015).

47. Svennerholm, A.-M. et al. Induction of mucosal and systemic immune responses against the common O78 antigen of an oral inactivated ETEC vaccine in Bangladeshi children and infants. Vaccine 40, 380-389 (2022).

48. Lee, C. H. & Tsai, C. M. Quantification of bacterial lipopolysaccharides by the purpald assay: measuring formaldehyde generated from 2-keto-3-deoxyoctonate and heptose at the inner core by periodate oxidation. Anal. Biochem. 267, 161-168 (1999).

49. Stark, J. C. et al. On-demand biomanufacturing of protective conjugate vaccines. Sci Adv 7, (2021).

50. Stark, J. C. et al. BioBits™ Bright: A fluorescent synthetic biology education kit. Sci Adv 4, eaat5107 (2018).

51. Çelik, E. et al. Glycoarrays with engineered phages displaying structurally diverse oligosaccharides enable high-throughput detection of glycan-protein interactions. Biotechnol. J. 10, 199-209 (2015).

52. Chen, L. et al. Outer membrane vesicles displaying engineered glycotopes elicit protective antibodies. Proc. Natl. Acad. Sci. U.S.A 113, E3609-18 (2016).

REFERENCES

1. U.S. Provisional Patent Application filed 20 Dec. 2013; Bundy B C, Smith M T. Lyophilized *Escherichia coli*-based Cell-free Systems for Robust, High-density, Long-term Storage.

2. U.S. patent application Ser. No. 16/357,820: Compositions and methods for rapid in vitro synthesis of bioconjugate vaccines in vitro via production and n-glycosylation of protein carriers in detoxified prokaryotic cell . . . M C Jewett, J C Stark, M P Delisa, T Jaroentomeechai.

(1) Karig, D. K.; Bessling, S.; Thielen, P.; Zhang, S.; Wolfe, J. Preservation of Protein Expression Systems at Elevated Temperatures for Portable Therapeutic Production. J. R. Soc. Interface 2017, 14 (129). https://doi.org/10.1098/rsif.2016.1039.

(2) Wilding, K. M.; Zhao, E. L.; Earl, C. C.; Bundy, B. C. Thermostable Lyoprotectant-Enhanced Cell-Free Protein Synthesis for on-Demand Endotoxin-Free Therapeutic Production. N. Biotechnol. 2019, 53, 73-80. https://doi.org/10.1016/J.NBT.2019.07.004.

(3) Gregorio, N. E.; Kao, W. Y.; Williams, L. C.; Hight, C. M.; Patel, P.; Watts, K. R.; Oza, J. P. Unlocking Applications of Cell-Free Biotechnology through Enhanced Shelf Life and Productivity of *E. Coli* Extracts. ACS Synth. Biol. 2020, 9 (4), 766-778. https://doi.org/10.1021/acssynbio.9b00433.

(4) Pardee, K.; Slomovic, S.; Nguyen, P. Q.; Lee, J. W.; Donghia, N.; Burrill, D.; Ferrante, T.; McSorley, F. R.; Furuta, Y.; Vernet, A.; et al. Portable, On-Demand Biomolecular Manufacturing. Cell 2016, 167 (1), 248-259.e12. https://doi.org/10.1016/j.cell.2016.09.013.

(5) Calhoun, K. A.; Swartz, J. R. An Economical Method for Cell-Free Protein Synthesis Using Glucose and Nucleoside Monophosphates. Biotechnol. Prog. 2005. https://doi.org/10.1021/bp050052y.

(6) Kim, H. C.; Kim, T. W.; Kim, D. M. Prolonged Production of Proteins in a Cell-Free Protein Synthesis System Using Polymeric Carbohydrates as an Energy Source. Process Biochem. 2011. https://doi.org/10.1016/j.procbio.2011.03.008.

(7) Cai, Q.; Hanson, J. A.; Steiner, A. R.; Tran, C.; Masikat, M. R.; Chen, R.; Zawada, J. F.; Sato, A. K.; Hallam, T. J.; Yin, G. A Simplified and Robust Protocol for Immunoglobulin Expression in <scp>E</Scp>Scherichia *Coli* Cell-free Protein Synthesis Systems. Biotechnol. Prog. 2015, 31 (3), 823-831. https://doi.org/10.1002/btpr.2082.

(8) Smith, M. T.; Berkheimer, S. D. Lyophilized *Escherichia Coli*-Based Cell-Free Systems for Robust, High-Density, Long-Term Storage. Biotechniques 2014, 56 (4), 186-193. https://doi.org/10.2144/000114158.

(9) Stark, J. C.; Jaroentomeechai, T.; Moeller, T. D.; Hershewe, J. M.; Warfel, K. F.; Moricz, B. S.; Martini, A. M.; Dubner, R. S.; Hsu, K. J.; Stevenson, T. C.; et al. On-Demand Biomanufacturing of Protective Conjugate Vaccines. Sci. Adv. 2021, 7 (6), eabe9444. https://doi.org/10.1126/sciadv.abe9444.

(10) Hershewe, J. M.; Warfel, K. F.; Iyer, S. M.; Peruzzi, J. A.; Sullivan, C. J.; Roth, E. W.; DeLisa, M. P.; Kamat, N. P.; Jewett, M. C. Improving Cell-Free Glycoprotein Synthesis by Characterizing and Enriching Native Membrane Vesicles. Nat. Commun. 2021, 12 (1). https://doi.org/10.1038/s41467-021-22329-3.

(11) Jaroentomeechai, T.; Stark, J. C.; Natarajan, A.; Glasscock, C. J.; Yates, L. E.; Hsu, K. J.; Mrksich, M.; Jewett, M. C.; Delisa, M. P. Single-Pot Glycoprotein Biosynthesis Using a Cell-Free Transcription-Translation System Enriched with Glycosylation Machinery. https://doi.org/10.1038/s41467-018-05110-x.

(12) Stenutz, R.; Weintraub, A.; Oran Widmalm, G. The Structures of *Escherichia Coli* O-Polysaccharide Antigens. https://doi.org/10.1111/j.1574-6976.2006.00016.x.

(13) Caschera, F.; Noireaux, V. A Cost-Effective Polyphosphate-Based Metabolism Fuels an All *E. Coli* Cell-Free Expression System. Metab. Eng. 2015, 27, 29-37. https://doi.org/10.1016/J.YMBEN.2014.10.007.

(14) Caschera, F.; Noireaux, V. Synthesis of 2.3 Mg/Ml of Protein with an All *Escherichia Coli* Cell-Free Transcription-Translation System. Biochimie 2014. https://doi.org/10.1016/j.biochi.2013.11.025.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cell-free protein synthesis (CFPS) reaction composition comprising:

(a) a cell lysate;

(b) maltodextrin at a concentration of 10-500 mg/mL;

(c) one or more buffer selected from HEPES, phosphate, and Bis-Tris;

(d) added nucleotide monophosphates (NMPs).

2. The composition of claim 1, wherein the composition does not comprise added phosphoenolpyruvic acid (PEP).

3. The composition of claim 1, wherein the composition does not comprise added coenzyme A (CoA), transfer RNA (tRNA) or nucleotide triphosphates (NTPs).

4. The composition of claim 1, wherein the composition comprises one or more of a transcription template and a translation template.

5. The composition of claim 1, wherein the cell lysate comprises an *E. coli* cell lysate.

6. The composition of claim 5, wherein the *E. coli* cell lysate comprises cell lysate based on BL21 strains.

7. The composition of claim 5, wherein the *E. coli* cell lysate comprises a Clm24 cell lysate.

8. The composition of claim 1 comprising additional mono-, di, or trisaccharides, wherein the additional mono-, di-, or trisaccharides, increase CFPS yields and/or reaction stability.

9. The composition of claim 1 comprising: about 60 mg/mL maltodextrin; HEPES pH 7.2; about 75 mM phosphate; about 10 mM Mg; and NMPs; and wherein the composition does not comprise added NTP, tRNA, CoA, and phosphoenolpyruvic acid (PEP).

10. The composition of claim 1, wherein the composition is lyophilized.

11. A kit comprising the composition of claim 10.

12. The kit of claim 11, wherein the kit is stored and/or transported at a temperature between room temperature and about 50° C. for up to four weeks.

* * * * *